(12) United States Patent
Franks et al.

(10) Patent No.: US 7,192,546 B2
(45) Date of Patent: Mar. 20, 2007

(54) METHODS OF FORMING SHAPED ARTICLES FROM SUSPENSIONS

(75) Inventors: George Vincent Franks, Dudley (AU); Stephen Bruce Johnson, Bendigo (AU); David Edwin Dunstan, West Brunswick (AU)

(73) Assignees: Commonwealth Scientific and Industrial Research Organisation, Canberra; Australian Food Industry Science Centre, Werribee; University of Melbourne, Parkville; Albright & Wilson (Australia) Limited, Yarraville; Tridan Limited, Melbourne; University of Newcastle, Callaghan (*) Notice: Subject to any disclaimer, the term of this patent is extended or adjusted under 35 U.S.C. 154(b) by 139 days.

(21) Appl. No.: 10/240,490

(22) PCT Filed: Apr. 6, 2001

(86) PCT No.: PCT/AU01/00395

§ 371 (c)(1),
(2), (4) Date: Apr. 1, 2003

(87) PCT Pub. No.: WO01/76845

PCT Pub. Date: Oct. 18, 2001

(65) Prior Publication Data

US 2003/0155689 A1 Aug. 21, 2003

(30) Foreign Application Priority Data

Apr. 7, 2000 (AU) .................................... PQ6772

(51) Int. Cl.
*B29C 39/02* (2006.01)
*B29C 45/00* (2006.01)

(52) U.S. Cl. ............... 264/319; 264/328.2; 264/328.18
(58) Field of Classification Search .................... None
See application file for complete search history.

(56) References Cited

U.S. PATENT DOCUMENTS 2,548,455 A * 4/1951 Walker et al. ............... 427/337
2,939,199 A   6/1960 Strivens (Continued)

FOREIGN PATENT DOCUMENTS

WO   WO 96/24077 A1   8/1996
WO   WO 99/59804 A1   11/1999

OTHER PUBLICATIONS

Johnson et al., Gel-forming of Advanced Ceramic Components, Ceramic Transactions (2001), 112 (Ceramic Processing Science VI), 471-476.*

(Continued)

*Primary Examiner*—Edmund H. Lee
(74) *Attorney, Agent, or Firm*—Wolf, Greenfield & Sacks, P.C.

(57) ABSTRACT

The invention relates to methods of forming shaped articles from suspensions which include ceramic or metallic powder, or from solutions or suspensions which include one or more pharmaceutical substances or other components. The method comprises the steps of: (a) combining solvent, polymer, cross-linking agent precursor and optional further components and placing into a mould of desired shape; (b) increasing temperature of mould contents to activate cross-linking agent; (c) allowing mould contents to solidify to sufficient extent to remove mould; (d) removing shaped article from the mould.

14 Claims, 21 Drawing Sheets

U.S. PATENT DOCUMENTS

Figure 1:
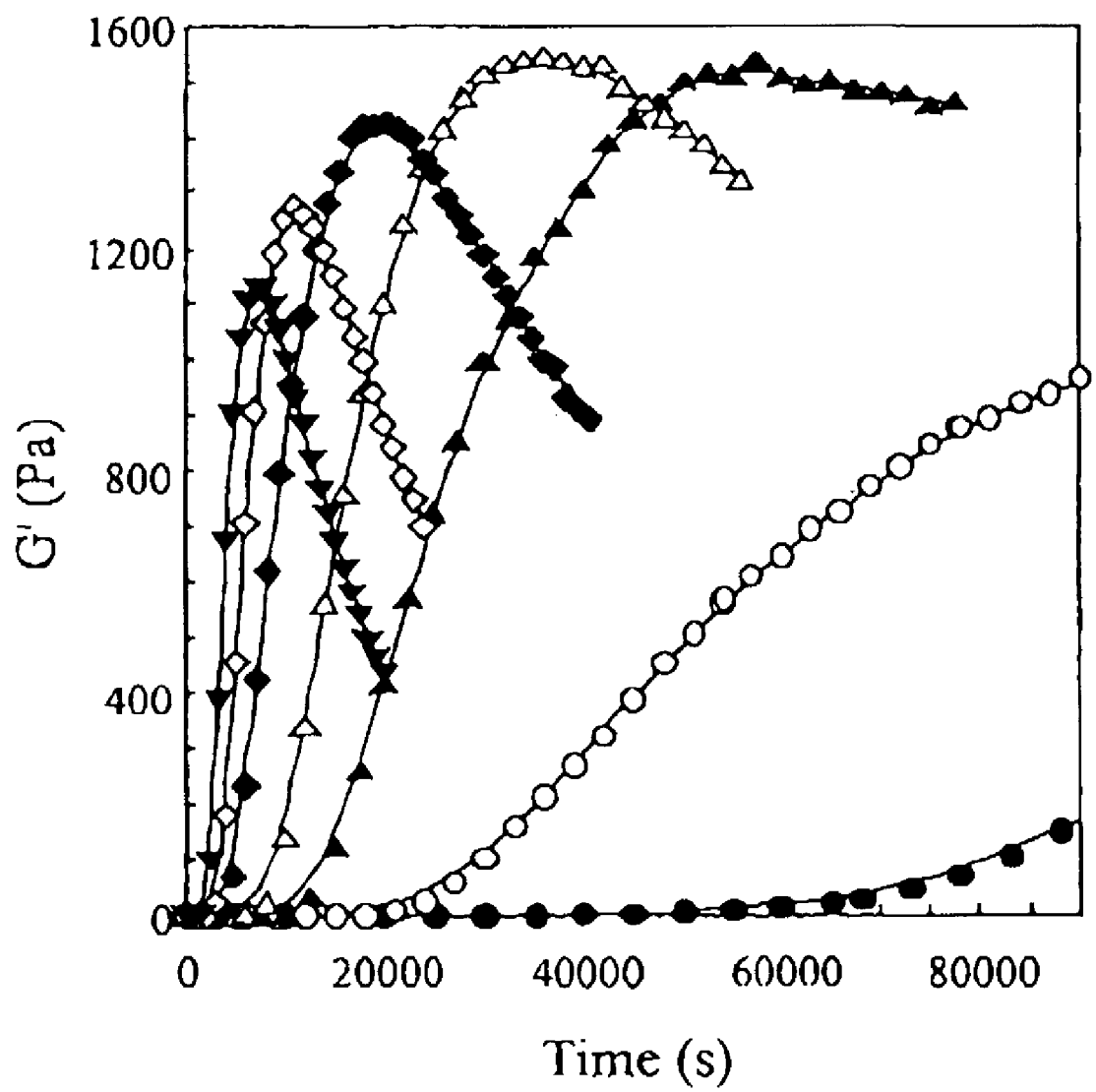

| | | | |
|---|---|---|---|
| 3,351,688 A | | 11/1967 | Kingery et al. |
| 4,011,291 A | | 3/1977 | Curry |
| 4,113,480 A | | 9/1978 | Rivers |
| 4,127,629 A | * | 11/1978 | Weaver et al. ............... 264/651 |
| 4,144,207 A | | 3/1979 | Ohnsorg |
| 4,264,661 A | * | 4/1981 | Brandolf ..................... 264/478 |
| 4,456,713 A | | 6/1984 | French et al. |
| 4,571,414 A | | 2/1986 | Renlund et al. |
| 4,734,237 A | | 3/1988 | Fanelli et al. |
| 4,894,194 A | | 1/1990 | Janney |
| 5,028,362 A | | 7/1991 | Janney et al. |
| 5,047,181 A | | 9/1991 | Occhionero et al. |
| 5,047,182 A | | 9/1991 | Sundback et al. |
| 5,135,690 A | * | 8/1992 | Imura et al. ................. 264/621 |
| 5,145,908 A | | 9/1992 | Jenny et al. |
| 5,242,646 A | * | 9/1993 | Torigoe et al. ............. 264/219 |
| 5,286,767 A | | 2/1994 | Rohrbach et al. |
| 5,338,888 A | * | 8/1994 | Paust et al. ................. 568/596 |
| 5,372,768 A | * | 12/1994 | Solomon ..................... 264/221 |
| 5,503,771 A | | 4/1996 | Staley et al. |
| 5,667,548 A | | 9/1997 | Graule et al. |
| 5,770,136 A | * | 6/1998 | Huang ........................ 264/101 |
| 5,788,891 A | | 8/1998 | Gauckler et al. |
| 5,948,335 A | | 9/1999 | Gauckler et al. |
| 6,017,976 A | * | 1/2000 | Reich et al. ................. 522/168 |

OTHER PUBLICATIONS

Usmanov, Z.U., Theory of Furan Polymer Preparation, Deposited Doc. (1972), VINITI 5646-73, ☐☐7 pp.*

Balzer, et al., "Coagulation Kinetics and Mechanical Behavior of Wet Alumina Green Bodies Produced via DCC", Journal of Colloid and Interface Science (1999), vol. 216, pp. 379-386.

Berthold, et al., Preparation and characterization of chitosan microspheres as drug carrier for prednisolone sodium phosphate as model for anti-inflammatory drugs, (1996), Journal of Controlled Release vol. 39, pp. 17-25.

Chen, et al., "Alumina Casting Based on Gelation of Gelatine", (1999), Journal of the European Ceramic Society, vol. 19, pp. 271-275.

German, Randall M. and Hens, Karl F., "Key Issues in Powder Injection Molding" Ceramic Bulletin (1991), vol. 70, No. 8, pp. 1294-1302.

Hansen, et al., "Reaction of poly(vinyl alcohol) and dialdehydes during gel formation probed by H n.m.r.-a kinetic study", Polymer (1997), vol. 38, No. 19, pp. 4863-4871.

Lange, Fred F., "Powder Processing Science and Technology for Increased Reliability", J. Am. Ceram. Soc., (1989), vol. 72, No. 1 pp. 3-15.

Mangels, John A., "Low-Pressure Injection Molding", American Ceramic Society Bulletin, (1994) vol. 73, No. 5. pp. 37-41.

Mathur, Nawal K. and Narang, Chander K., "Chitin and Chitosan, Versatile Polysaccharides from Marine Animals", Journal of Chemical Education, (1990) vol. 67, No. 11, pp. 938-942.

Pujari, Vimal K. et al., "Reliable Ceramics for Advanced Heat Engines", American Ceramic Society Bulletin (1995), vol. 74, No. 4, pp. 86-90.

Takeshita, Masaaki and Kurita, Sumihiko, "Development of Self-Hardening Slip Casting",Journal of the European Ceramic Society (1997) vol. 17, pp. 415-419.

Thanoo, et al., Cross-linked Chitosan Microspheres: "Preparation and Evaluation as a Matrix for the Controlled Release of Pharmaceuticals", (1992) J. Pharm Pharmacol. vol. 44, pp. 283-286.

* cited by examiner

METHODS OF FORMING SHAPED ARTICLES FROM SUSPENSIONS

FIELD OF THE INVENTION

The present invention relates to methods of forming shaped articles and in particular, but not exclusively, to methods of forming shaped articles from suspensions which include ceramic or metallic powder or from solutions or suspensions which include one or more pharmaceutical substances or other components. The shaped articles which include one or more pharmaceutical substances can be employed as pharmaceutical controlled release formulations.

BACKGROUND OF THE INVENTION

It is impractical to cast ceramics from the molten state as is commonly done with many metal alloys. This is primarily due to the requirement of a highly refined defect free microstructure necessary to produce reliable components with properties for high performance applications. Furthermore the high melting temperature and/or decomposition of the material makes melting impossible or economically impractical.

High performance ceramic materials thus must be made from fine powders that sinter (densify) at a temperature below their melting point. The reduction in free surface energy is the driving force for the elimination of porosity and the densification.

Ceramics are inherently brittle materials and are thus sensitive to flaws which reduce the strength and reliability of the final article. The strength (S) depends on the fracture toughness of the material ($K_{IC}$) and the size of the flaw or crack (c) as follows: $S=YK_{IC}/\sqrt{c}$. The fracture toughness is a material property and Y a geometric factor that depends upon the details of the flaw shape. Large flaws and cracks greatly reduce tile strength of the material.

Current forming processes such as dry pressing result in inhomogeneous green density, which results in flaws that reduce strength and reliability. The dry processing technique is deficient in that there is no capacity to de-agglomerate the dry powder and remove flaws from the powder that may exist in the as received raw material, or were accidentally added to the powder during processing.

Wet colloidal processing can be used to overcome the deficiencies of dry powder processing. The colloidal method may be used to break down agglomerates and remove flaws via filtration, sedimentation or other means to produce nearly defect free uniform density green bodies. This results in improved strength and reliability of the final component (Lange 1989, Pujari 1995).

Ceramics are extremely hard materials and thus are difficult to machine. Expensive diamond grinding is often required in order to finish articles produced by known methods. Thus it is economically advantageous to produce a component which does not require, or requires only minimal machining. Processes which do not require machining after forming of the shaped article are known as net shape processes and constitute the most desirable approach.

Several methods of producing near net shaped ceramic and metal articles from powders currently exist. Although useful for some applications many of these processes have some disadvantages compared to the present invention.

Thermoplastic injection of powders with binders that melt have been known for more than 30 years (U.S. Pat. No. 3,351,688). These methods utilise binders such as paraffin wax (U.S. Pat. No. 4,011,291), thermoplastic polymeric resins (U.S. Pat. No. 4,144,207), and more recently polymer mixtures (U.S. Pat. No. 4,571,414) which are molten at high temperature and solidify at lower temperature within the mould cavity. These methods have several limitations and problems. Firstly, since they solidify upon cooling the part may slump or loose its shape on the further reheating needed for binder removal and sintering. The removal or burnout of the large quantities of binders used in these methods generally results in lengthy and costly heat treatments, cracking, distortion, and generally low quality components (German et al. 1991). Furthermore, many of these processes utilise equipment originally designed for plastics manufacture. The use of abrasive ceramic particles in these metal devices which are operated under high pressure, results in wear of the equipment and detrimental metallic inclusions in the article. Systems that utilise thermosetting binders such as epoxies (U.S. Pat. No. 2,939,199, U.S. Pat. No. 4,456,713, Takeshita et al. 1997) suffer from many of the same problems, particularly including lengthy and detrimental binder burnout processes.

Low pressure injection moulding (Mangels 1994) processes may alleviate at least the abrasion problem associated with the high pressure injection moulding processes, but by itself does not address the binder problems. The Quickset injection moulding process, (U.S. Pat. Nos. 5,047,181, 5,047,182) utilises a low pressure injection moulding (or pourable) process with only a few percent of a binder in either aqueous or non-aqueous solvents. This method utilises the freezing of the suspending medium as the method of changing the suspension behaviour from liquid-like to solid-like. This system has the advantage that the solidification can occur very quickly. The disadvantage of this system is that it requires a lengthy and costly (sublimative) freeze drying process since the parts would melt and lose shape if heated under atmospheric pressure during drying. The advantage of the above mentioned thermoplastic and low pressure injection moulding formulations is that temperature may be used as a switch mechanism for controlling the suspension behaviour as either a liquid-like or a solid-like maternal.

Recently another pourable or low pressure injection mouldable process which utilises an aqueous system has been disclosed (U.S. Pat. Nos. 5,667,548, 5,788,891, 5,948,335, Balzer et al., 1999). This method relies on a chemically activated change in solution conditions that change the particle-particle interaction from repulsive to attractive. This process requires particularly long retention times in the mould to achieve strength sufficient to successfully remove the mould. The published results indicate that it takes 24 hours for the articles to achieve a strength of about 8 kPa. (Balzer et al. 1999) With this system, once all the components are added to the suspension the gelation begins and proceeds even at room temperature, although the rate is much slower than when the temperature is increased. In practice it is difficult to produce a suspension which will remain liquid-like for a sustained period at room temperature, and gel quickly at elevated temperature.

Janney and coworkers (U.S. Pat. Nos. 4,894,194, 5,028, 362, 5,145,908) disclose a process which utilises the polymerisation of a monomer in the suspension solution via a free radical initiator. This process produces strong de-mouldable bodies relatively quickly. There is only a relatively small amount of the polymer in the green body (article before firing) so it is relatively easy to burn out. Unfortunately most of the monomer-initiator systems suitable for the process are somewhat toxic. The mechanical behaviour of bodies produced with this method indicate very limited flexibility and thus may be fractured when large strains are applied to the component during de-moulding.

Methods suitable for filling moulds via low pressure injection moulding or pouring that utilise aqueous solutions of gelling bio-polymers have also been disclosed. These methods (U.S. Pat. Nos. 4,734,237, 5,286,767, 5,503,771, Chen et al. 1999,) generally utilise physical gelation of bio-polymers such as agar, alginate, gelatine, or pectin. These systems gel when the temperature is decreased, and the gelation is reversible. The disadvantage of these types of systems is that they will re-liquefy when heated again for instance during drying and sintering of the part. The method disclosed by Rivers (U.S. Pat. No. 4,113,480) utilises methylcellulose, which gels as the temperature is increased. All these methods rely on the gelation to proceed by a mechanism in which the polymer chains form intertwined coils held together by physical bonds. With these methods the polymer chains are not chemically cross-linked.

No previously disclosed method describes a polymer cross-linked with a temperature activated cross-linking agent for forming shaped articles, particularly from powders. Although the invention was originally conceived in the context of ceramic gel casting, the present inventors have also found application for their work in the production of pharmaceutical controlled release formulations and shaped articles containing other components. The present invention allows the encapsulation of pharmaceutical substances which can be released at a controlled rate following administration. The adoption of this technology in the preparation of pharmaceutical controlled release formulations has the advantage of allowing thorough mixing of the pharmaceutical substance within the gel forming mixture with the ability to readily manipulate gel strength and thus also the rate of pharmaceutical substance release.

It is with the above background in mind that the present invention has been conceived.

SUMMARY OF THE INVENTION

According to one embodiment of the present invention there is provided a method of forming a shaped article comprising the steps of:
  (a) combining solvent, polymer, cross-linking agent precursor and optional further components and placing into a mould of desired shape;
  (b) increasing temperature of mould contents to activate cross-linking agent;
  (c) allowing mould contents to solidify to sufficient extent to remove mould;
  (d) removing shaped article from the mould.

In preferred embodiments of the invention the polymer may be selected from the group chitosan, polyvinylalcohol, chitin, polyacrylic acid, polyvinylacrylate, polyacrylate, polyacrylamide, pectin, xanthan gum, polymers having amide, amine, carboxylic acid and/or hydroxyl functionalities, and mixtures thereof.

Preferably the cross-linking agent precursor forms a multifunctional aldehyde upon temperature increase and particularly preferably the cross-linking agent precursor forms a di-aldehyde upon temperature increase.

In a preferred embodiment of the invention the cross-linking agent precursor is 2,5-dimethoxy-2,5-dihydrofuran (DHF).

The mould may be filled by pouring or by injection of components into the mould. Preferably the injection will be low pressure injection moulding.

In preferred embodiments of the invention the solvent is selected from water, ethanol, methanol, iso-propanol and mixtures thereof.

In preferred embodiments of the invention the optional further components include ceramic or metallic powders. For example the ceramic or metallic powder is selected from alumina, zirconia, silica, silicon nitride, silicon carbide, aluminium nitride and mixtures thereof.

In another aspect of the invention the optional further components include one or more pharmaceutical substances.

In a particularly preferred embodiment of the invention the process as outlined above includes further drying and/or firing steps.

In another embodiment of the invention the optional further components include one or more of dispersants, chelating agents, surfactants, salts, colouring agents and biologically active agents.

In a particularly preferred embodiment the shaped article is net shape or near net shape.

In a still further embodiment the invention relates to shaped articles produced according to the methods outlined above.

BRIEF DESCRIPTION OF THE FIGS.

The present invention will be further described, by way of example only, with reference to the figures which show as follows:

FIG. 1. The storage modulus of a 1.5 wt % chitosan/2.5× $10^{-2}$ mole dm$^{-3}$ DHF solution at pH=1.4 as a function of temperature and time. ●=40° C.; ○=50° C.; ▲=60° C.; Δ=70° C.; ◆=80° C.; ◇=90° C.; ▼=98° C.

Figure 2:
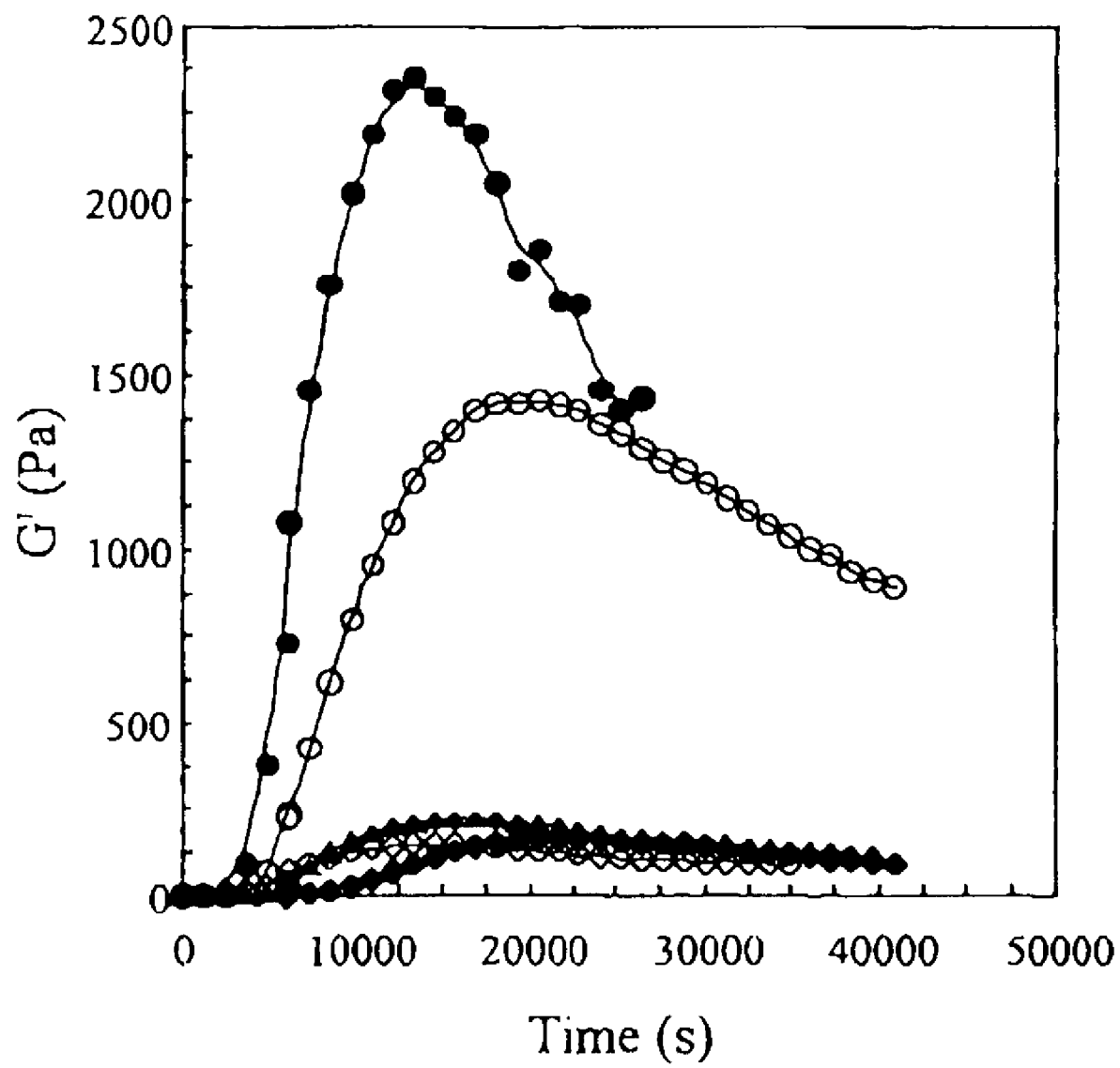

FIG. 2. The storage modulus of a 1.5 wt % chitosan/2.5× $10^{-2}$ mole dm$^{-3}$ DHF solution as a function of both time and several pH conditions. The temperature was 80° C. The pH was ●=0.9; ○=1.4; ▲=2.1; ◇=3.1; ◆=3.9.

Figure 3:
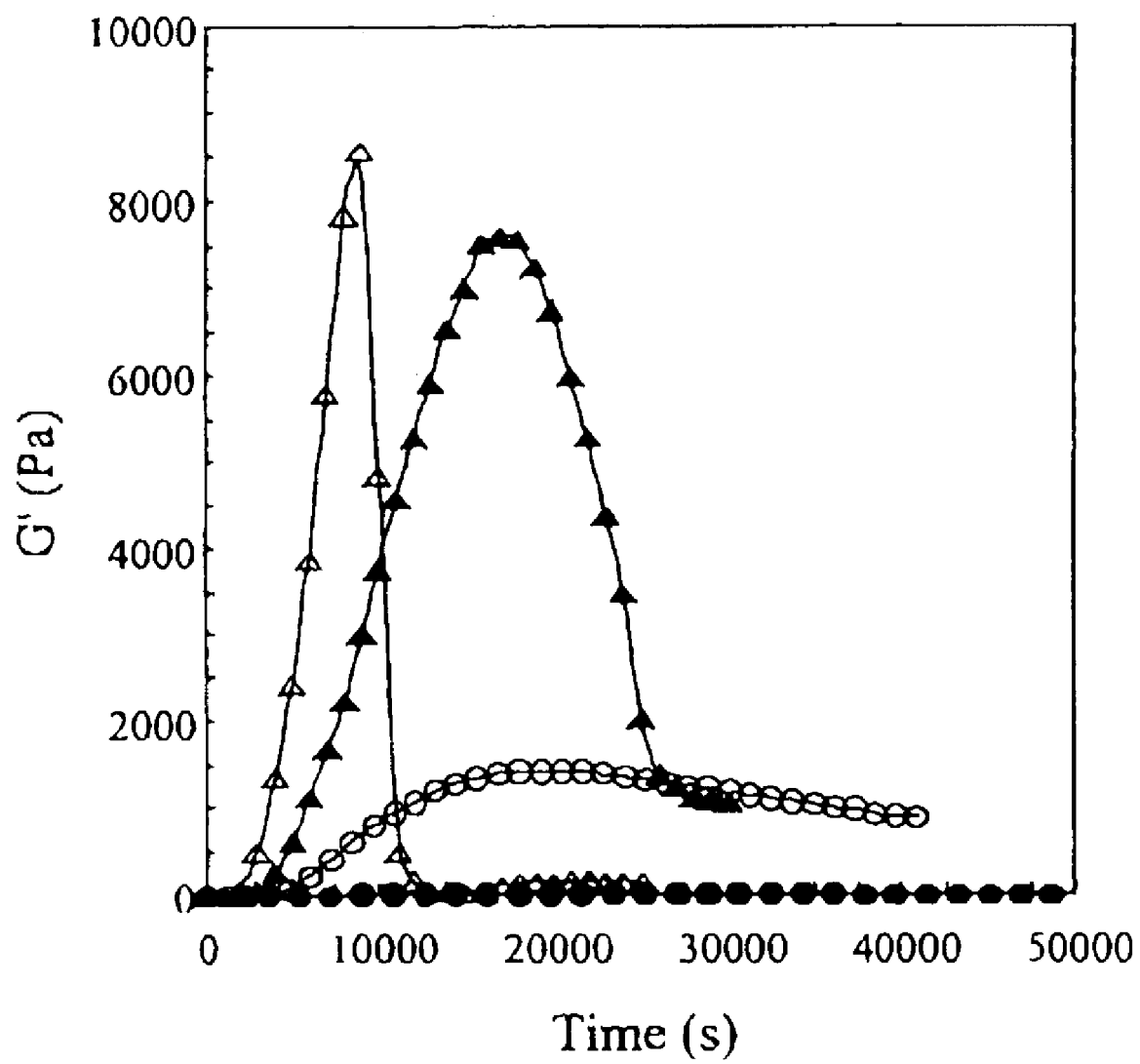

FIG. 3. The storage modulus of a 1.5 wt % chitosan solution at pH=1.4 as a function of both DHF concentration and time. The temperature was 80° C. The DHF concentration was ●=1.0×10$^{-2}$ mole dm$^{-3}$; ○=2.5×10$^{-2}$ mole dm$^{-3}$, ▲=5.0×10$^{-2}$ mole dm$^{-3}$; Δ=1.0×10$^{-1}$ mole dm$^{-3}$.

Figure 4:
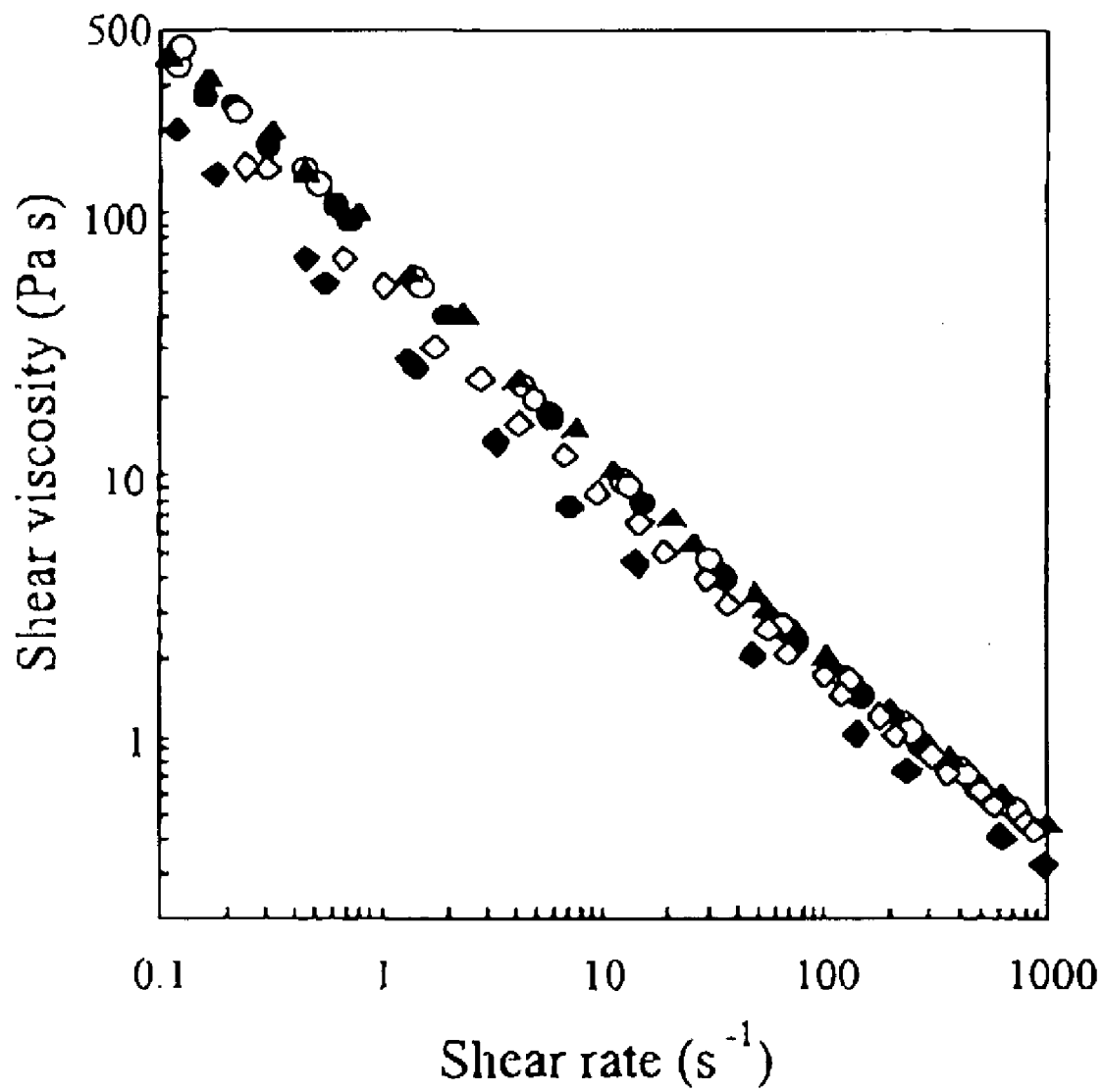

FIG. 4. Viscosity verses shear rate for a 45 v % AKP-30 alumina suspension in a 1.0wt % (per solution weight) solution at 20° C. at pH ●=1.1; ○=1.4; ▲=2.2; ◇=3.2; ◆=4.5.

Figure 5:
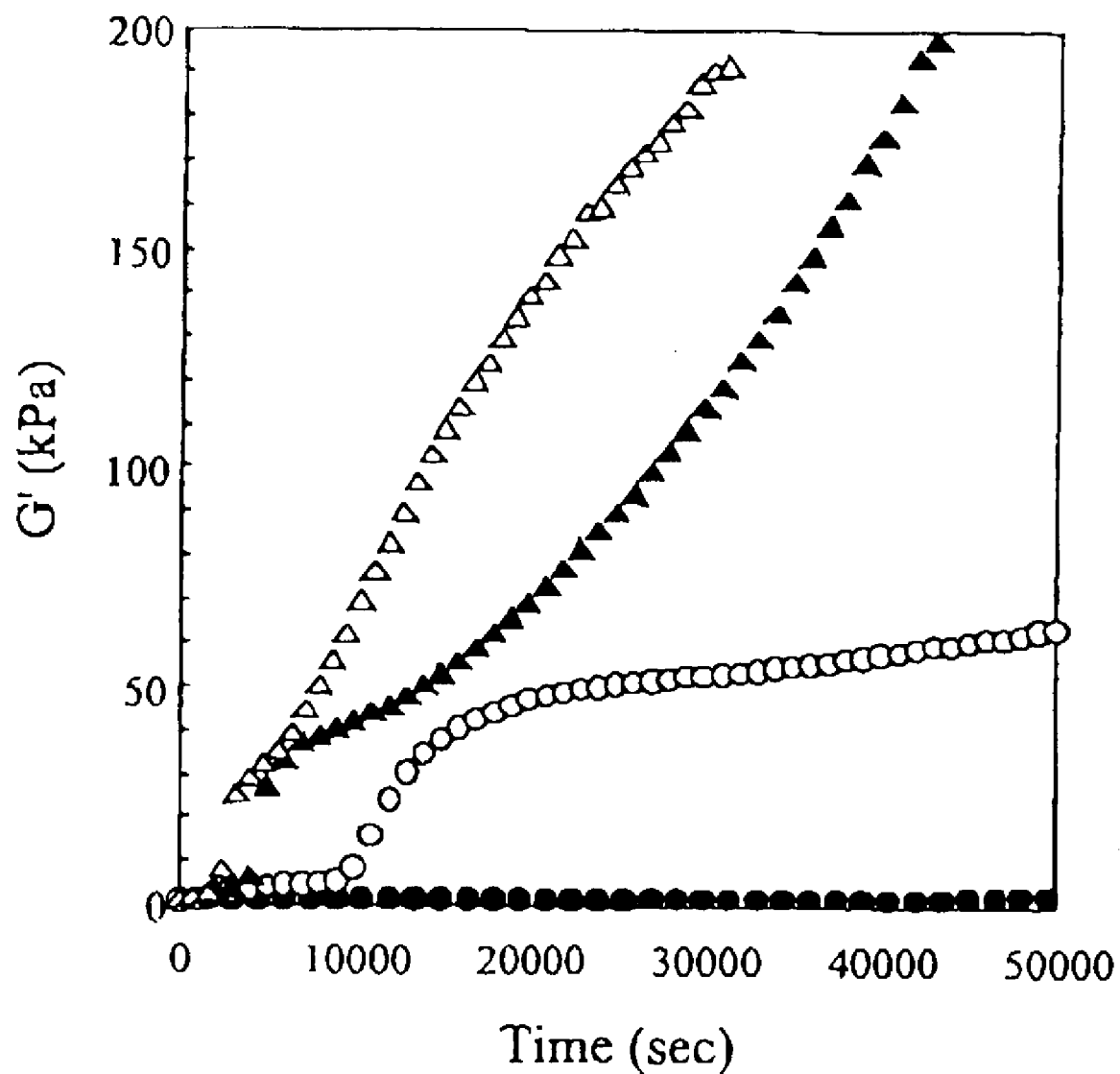

FIG. 5. Shear modulus as a function of time for 45 V % alumina suspensions in 1.0 wt % chitosan solutions with 100 mM DHF at pH 2.2, at various temperatures. ●, 20° C.; ○, 60° C.; ▲, 80° C.; Δ, 98° C.

Figure 6:
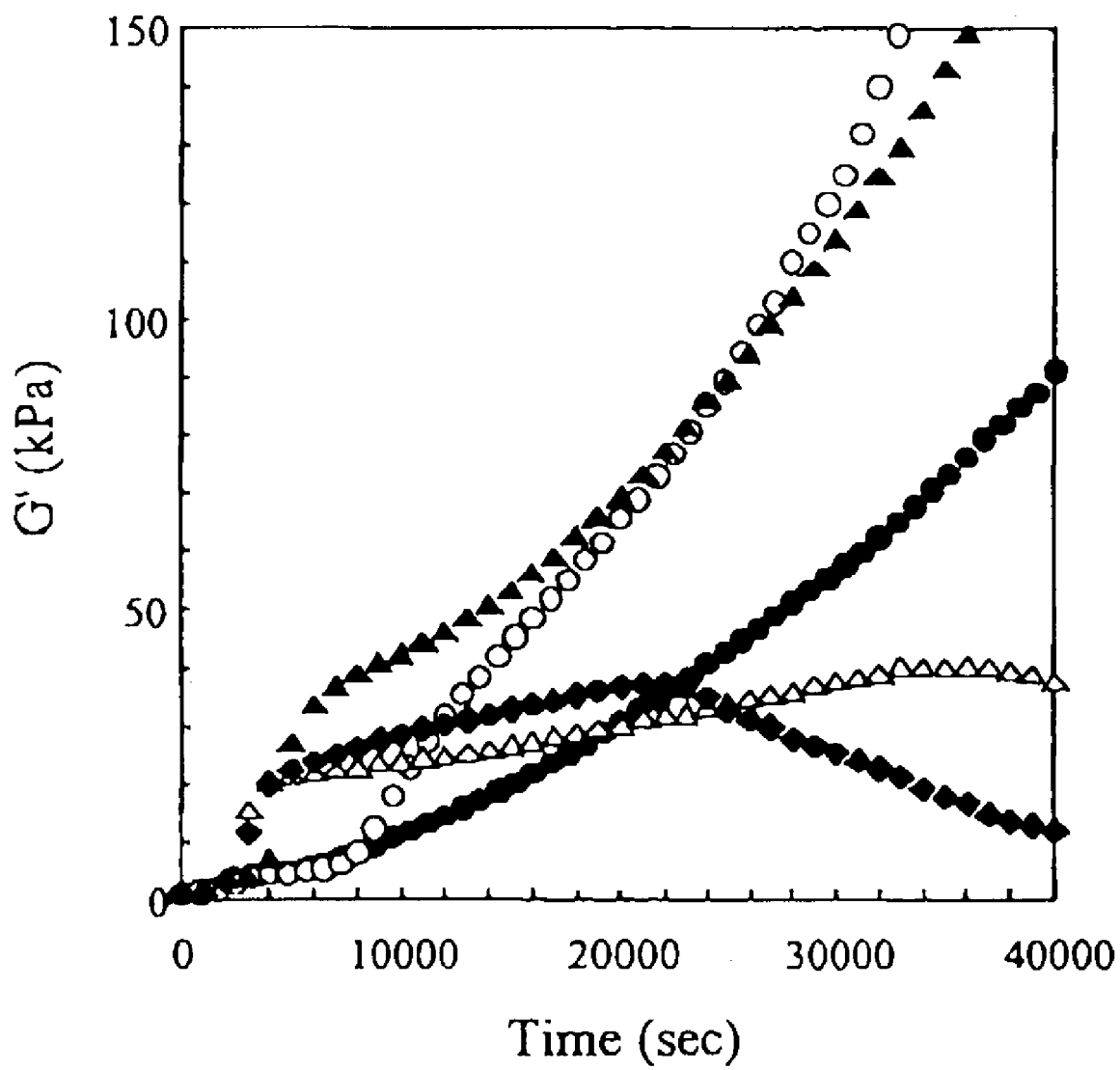

FIG. 6. Shear modulus as a function of time for a 45 v % AKP-30 alumina suspension in a 1.0 wt % (per solution weight) solution with 100 mM DHF at 80° C. at pH ●=1.1; ○=1.4; ▲=2.2; Δ=3.2; ◆=4.5.

Figure 7:
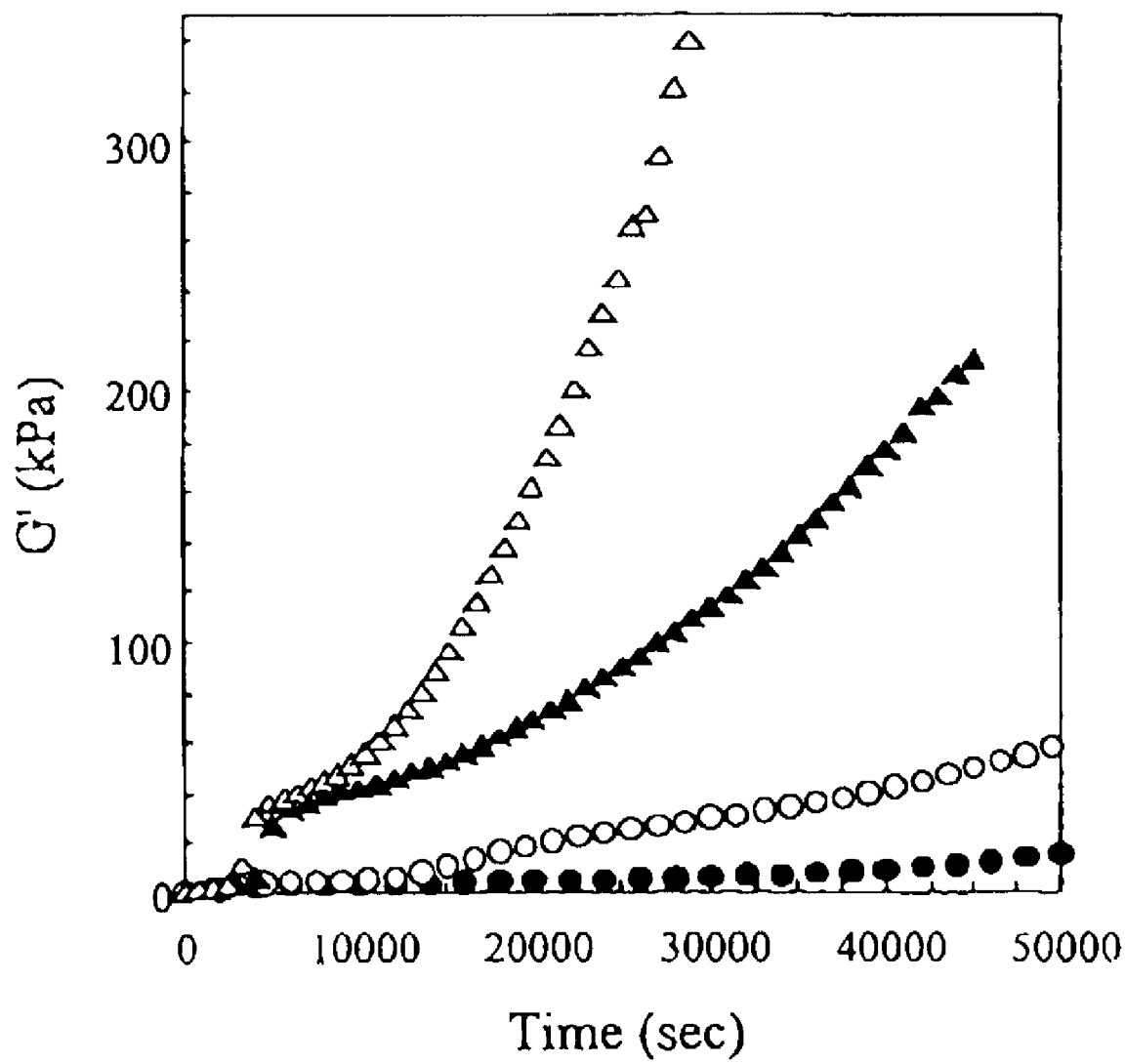

FIG. 7. Shear modulus as a function of time for a 45 v % AKP-30 alumina suspension in a 1.0 wt % (per solution weight) solution at pH 2.2 at 80° C. with various DHF concentrations ●=20 mM; ○=50 mM; ▲=100 mM; Δ=200 mM.

Figure 8:
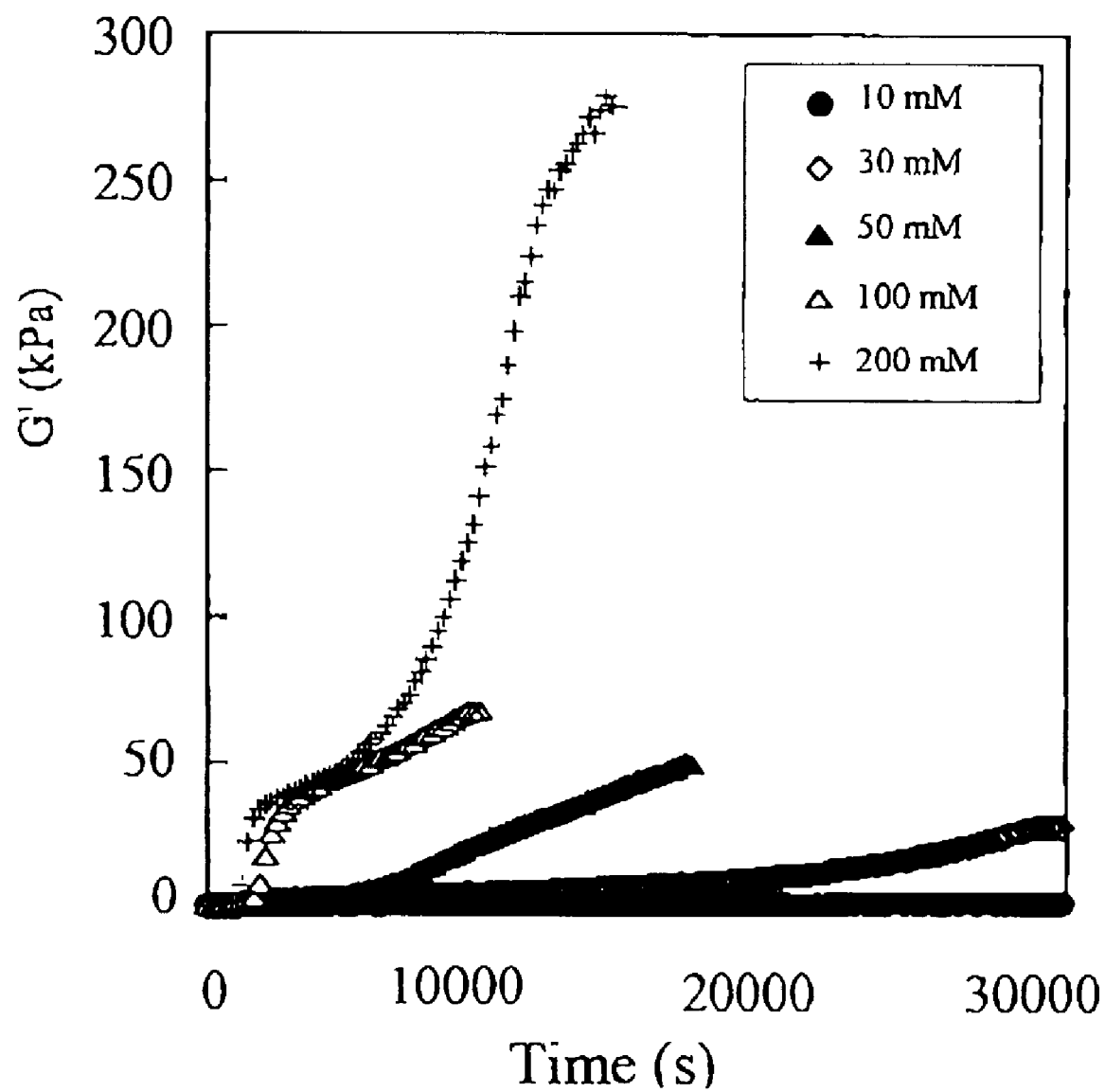

FIG. 8. Shear modulus as a function of time for a 40 v % AKP-30 alumina suspension in a 0.5 wt % (per solution weight) solution at pH 2.9 at 90° C. with various DHF concentrations ●=10 mM; ◇=30 mM; ▲=50 mM; Δ=100 mM; +=200 mM.

Figure 9:
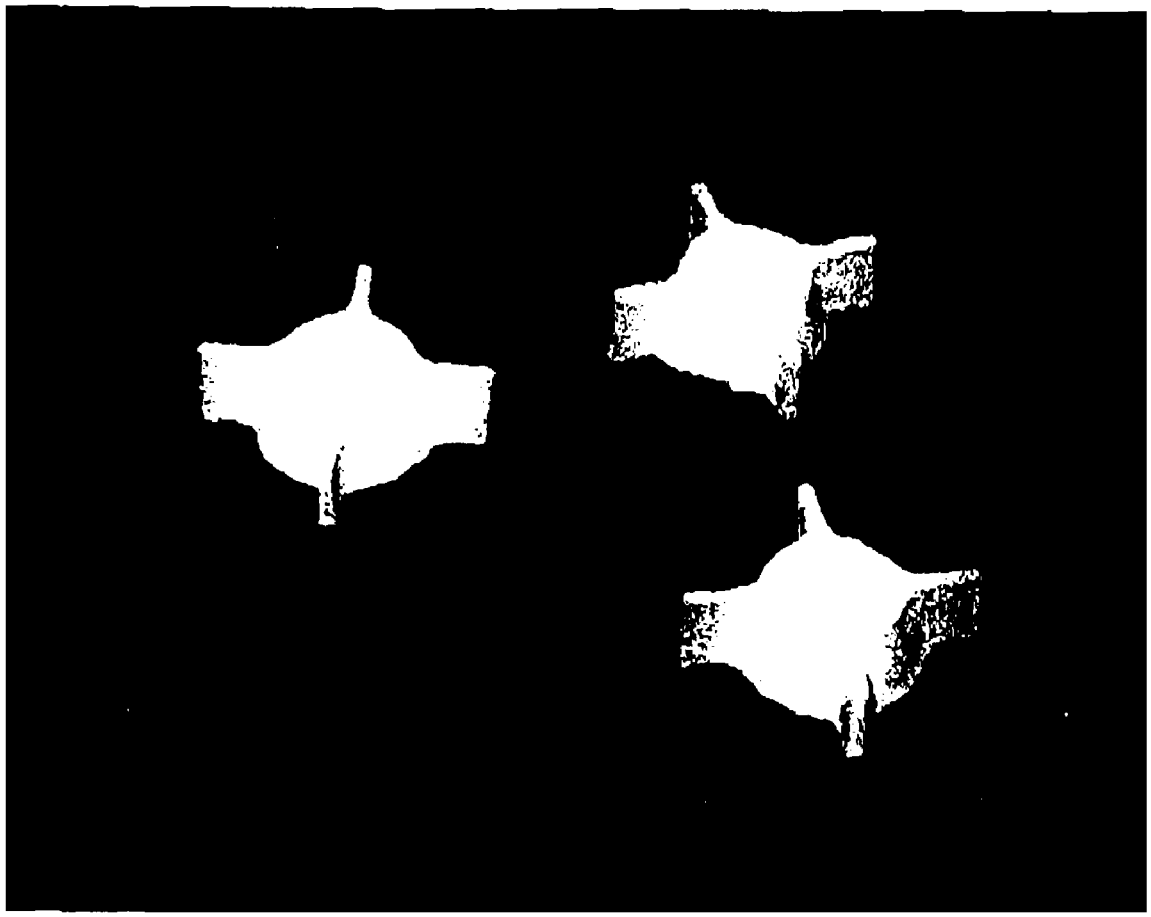

FIG. 9. Photograph of three fired pseudo-rotors produced according to the invention.

Figure 10:
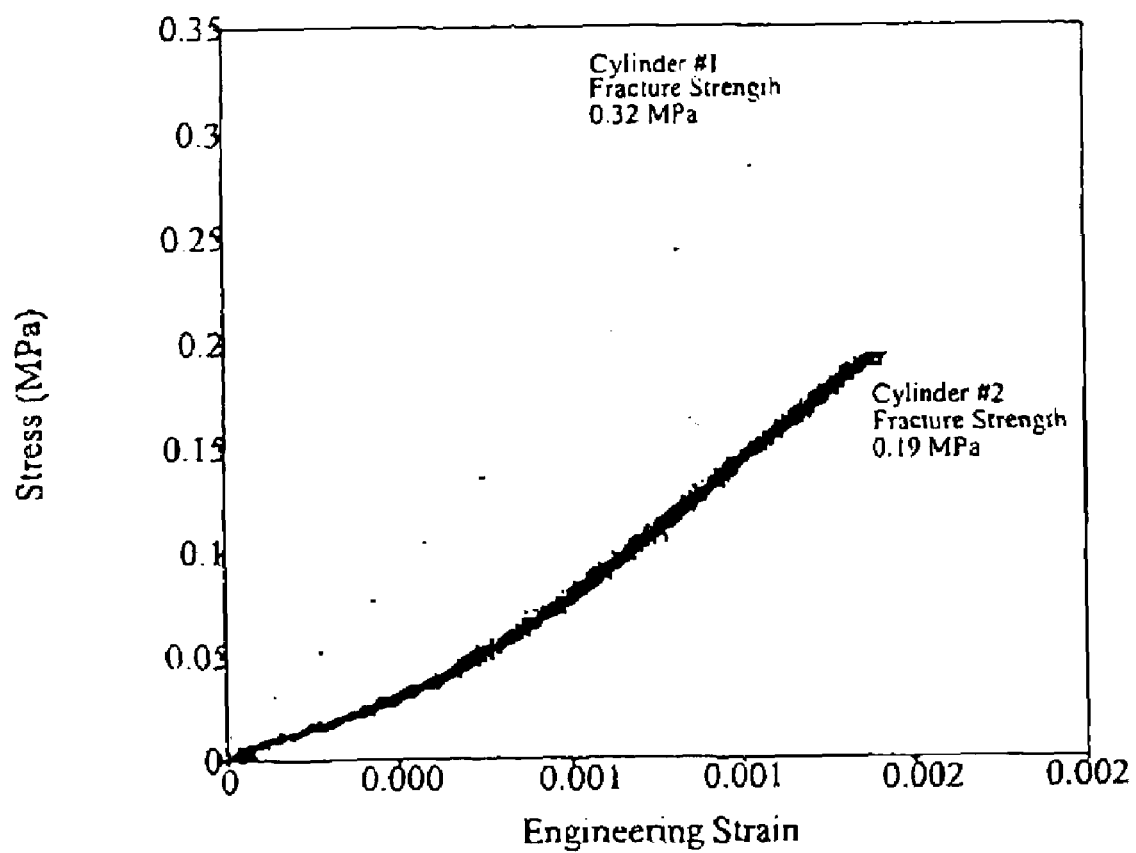

FIG. 10. Stress-engineering strain behaviour and fracture strength of dried green bodies produced according to the invention.

Figure 11:
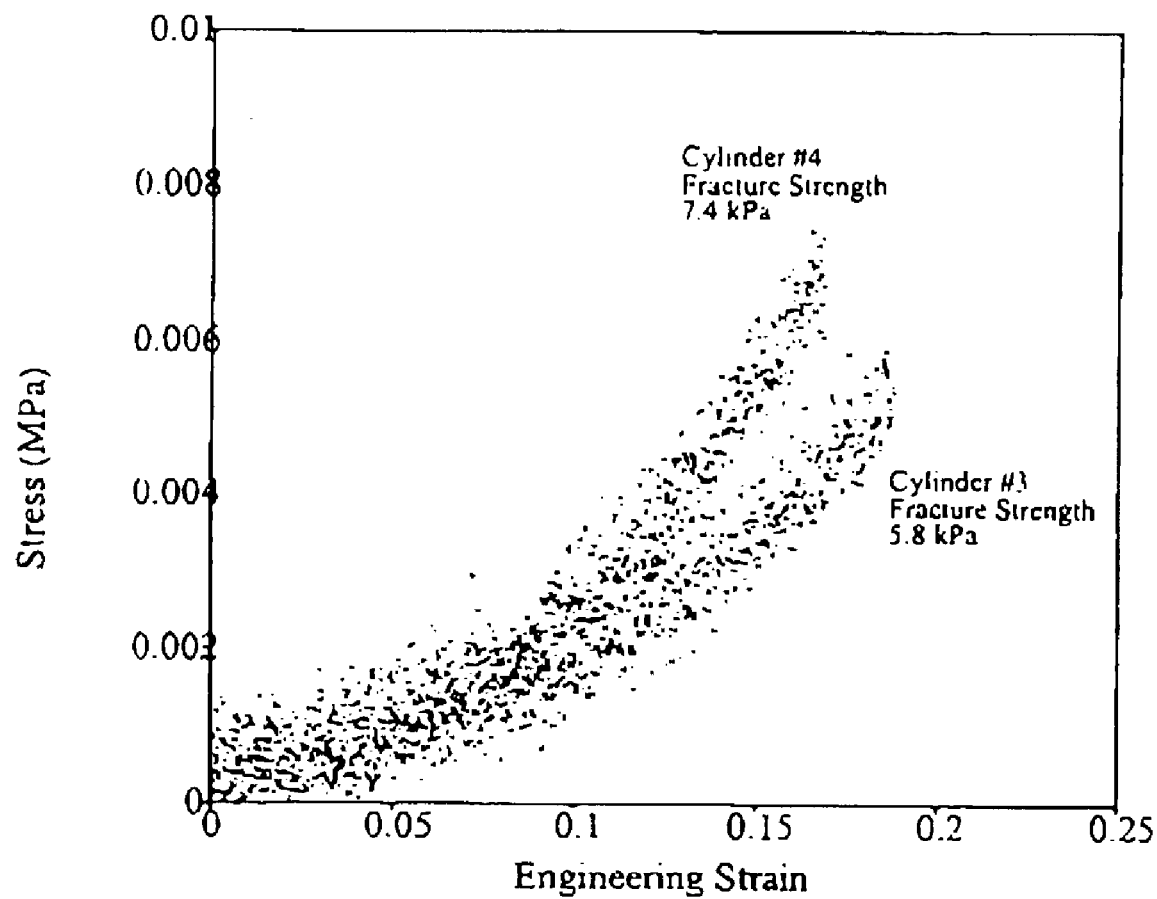

FIG. 11. Stress-engineering strain behaviour and fracture strength of wet gelled bodies produced according to the invention. Notice particularly the large strain to failure ratio of the bodies.

Figure 12:
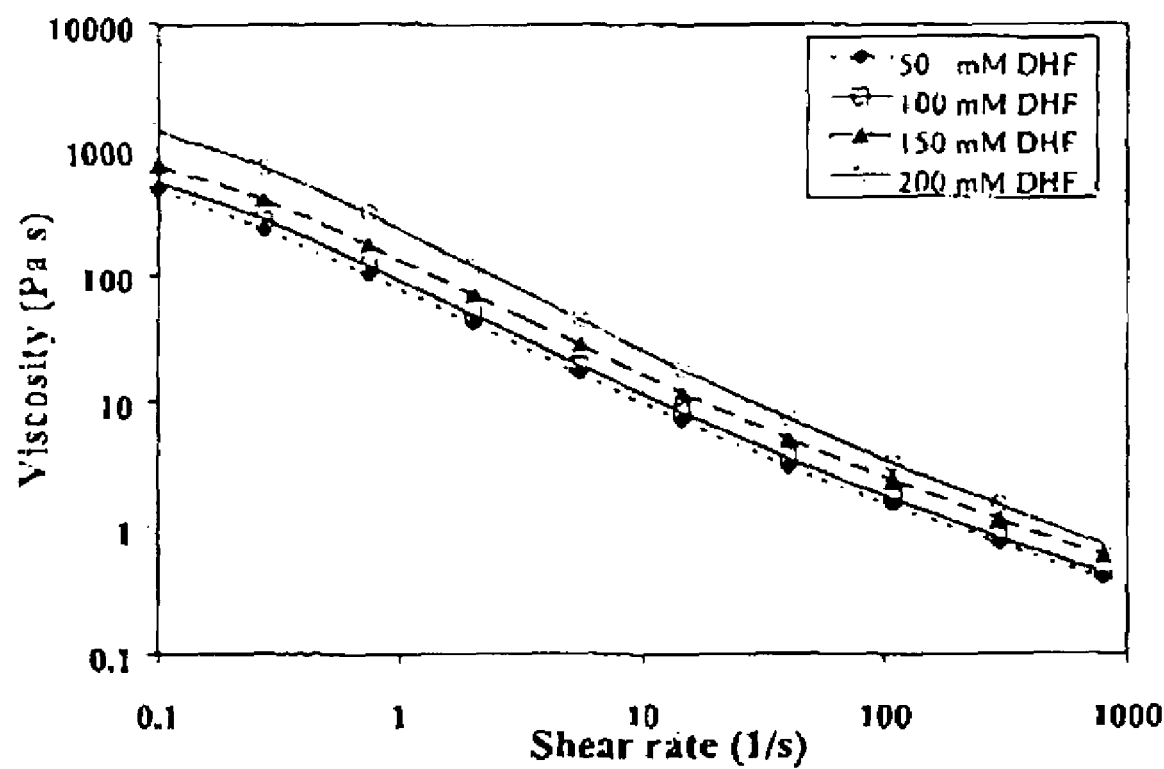

FIG. 12. Viscosity verses shear rate of gelcasting suspensions containing 45 V % alumina, 1.0 wt % (by solution wt.) chitosan, at pH 2.2 and 25° C., with different concentrations of DHF as indicated. Measurements taken two hours after the addition of DHF.

Figure 13:
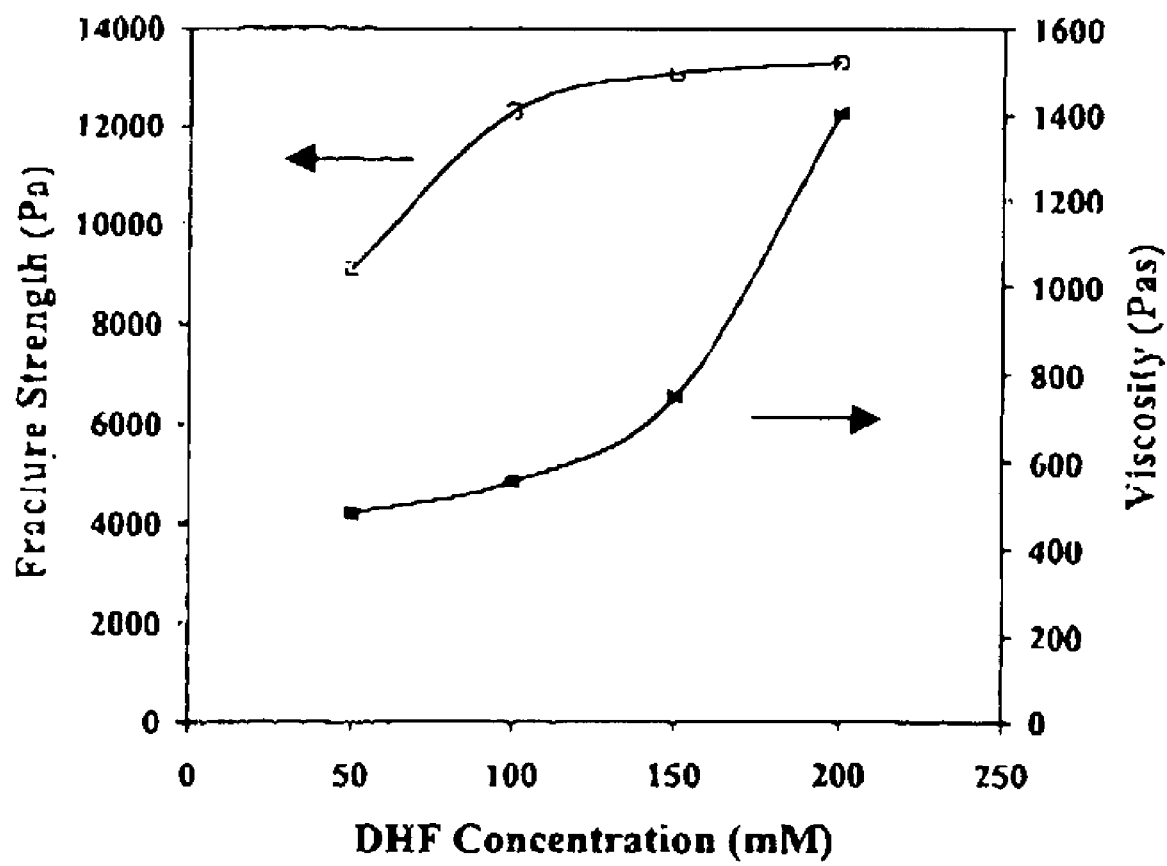

FIG. 13. Effect of DHF concentration on the viscosities (at $0.1\ s^{-1}$) of suspensions prior to gelation and the strength of bodies after gelation. Data transcribed from FIGS. 12 and 14.

Figure 14:
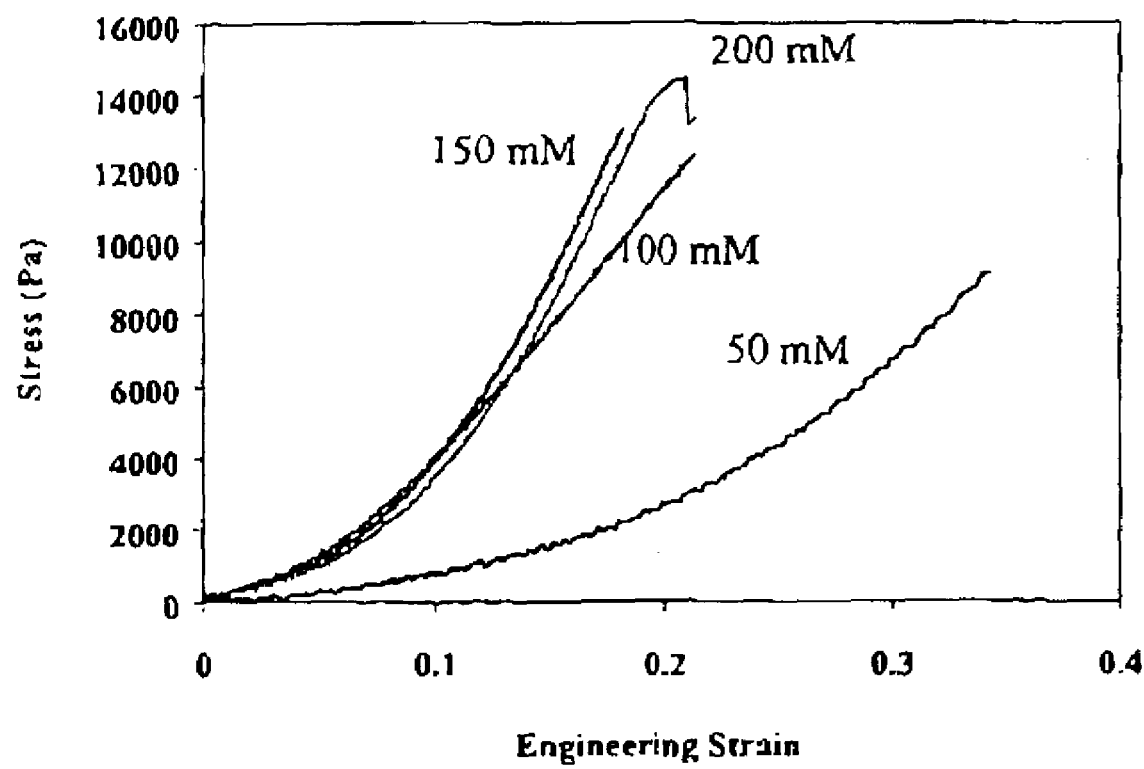

FIG. 14. Stress verses strain relationship for cylinders tested in diametral compression containing various concentrations of crosslinker (DHF) as indicated. All four bodies were made from suspensions containing 45 V % alumina, 1.0 wt % (by solution wt.) chitosan, at pH 2.2 that were gelled at 85° C. for 30 mins.

Figure 15:
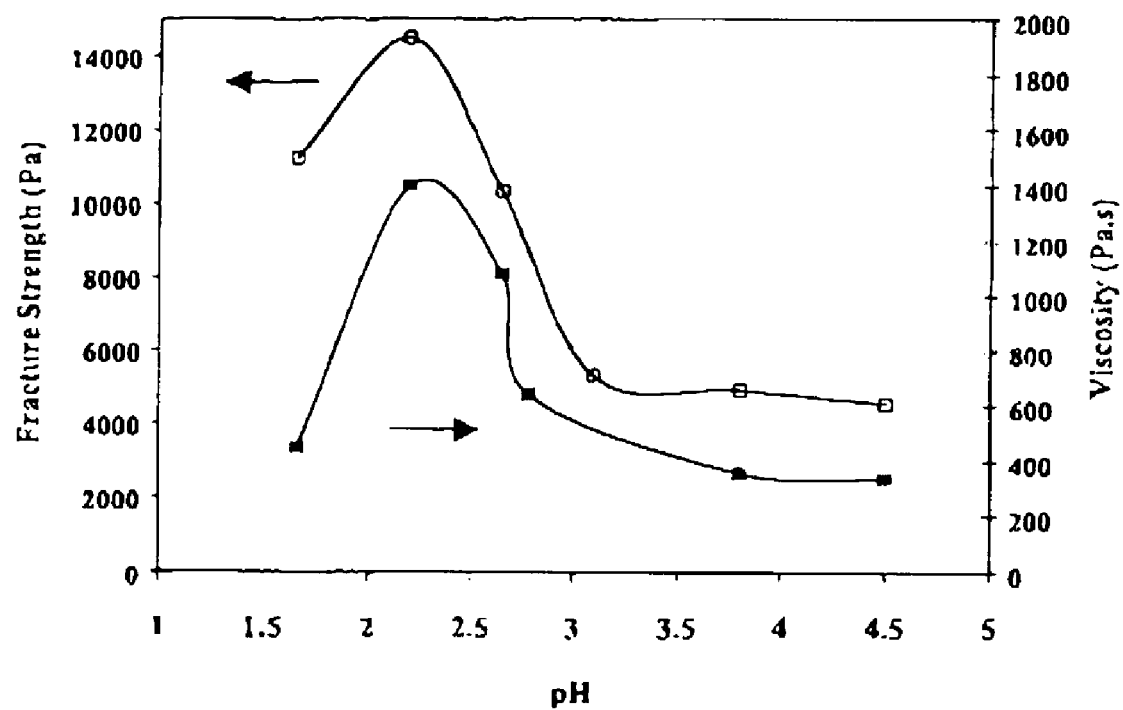

FIG. 15. Effect of pH on the viscosity (at 25° C. and 0.1 s−1) of suspensions prior to gelation and the strength of the body after gelation. The suspensions contained 45 V % alumina, 1.0 wt % (by solution wt.) chitosan, 200 mM DHF, and were gelled at 85° C. for 30 mins.

Figure 16:
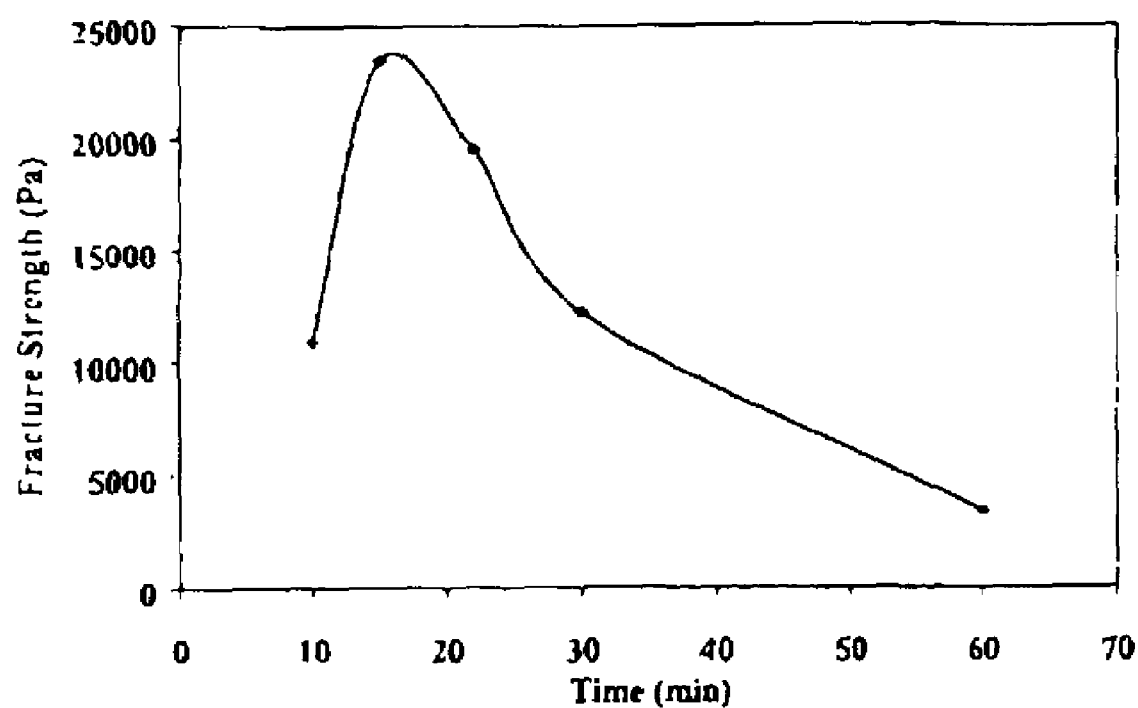

FIG. 16. Effect of heat treatment time on the strength of wet gelled bodies. The suspensions contained 45 V % alumina, 1.0 wt % (by solution wt.) chitosan, 100 mM DHF, at pH 2.2 and were gelled at 85° C. for the indicated times.

Figure 17:
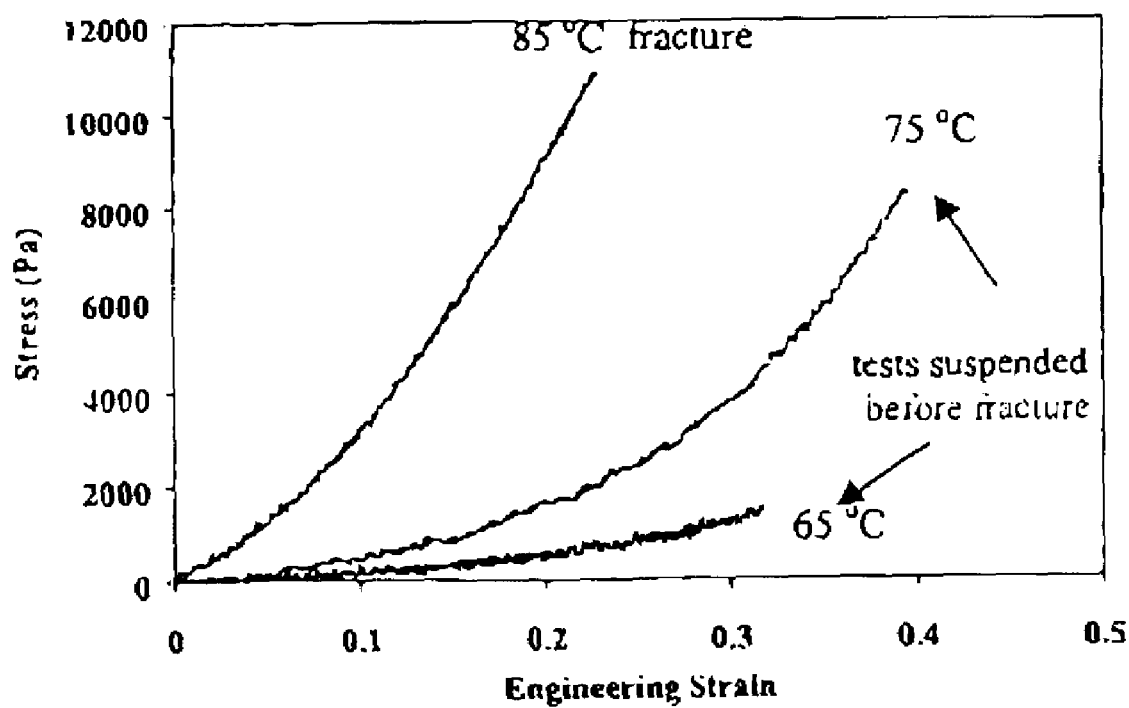

FIG. 17. Stress-strain behaviour of cylinders made from suspensions containing 45 V % alumina, 1.0 wt % (by solution wt.) chitosan, 100 mM DHF, at pH 2.2 heat treated for 30 mins. at the indicated temperatures.

Figure 18:
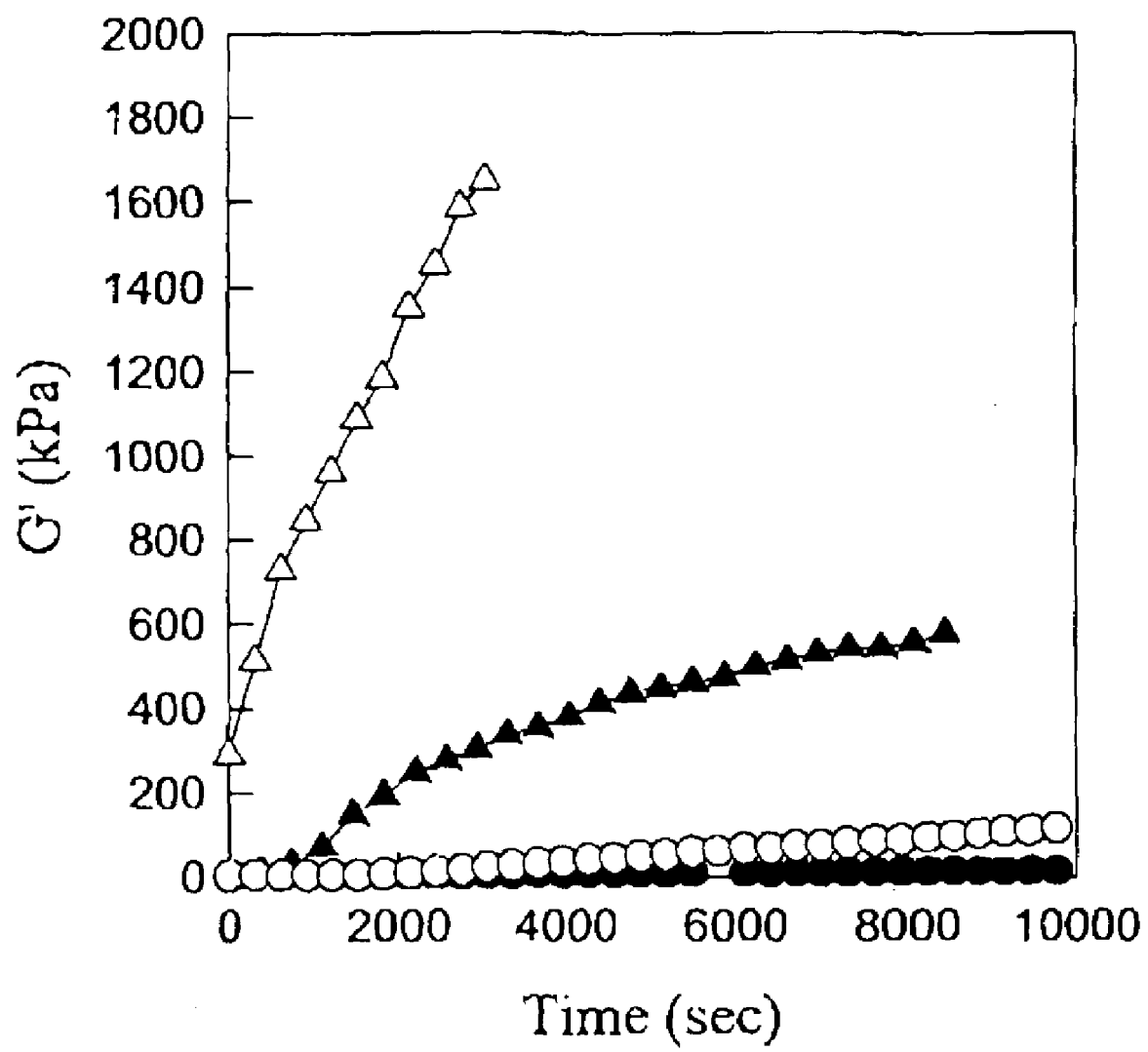

FIG. 18. Shear modulus as a function of time for a 30 v % Zirconia suspension in a 1.0 wt % chitosan solutions with 80 mM DHF at pH 2.2 at various temperatures ● 20° C., ○ 60° C. ▲ 80° C., Δ 98° C.

Figure 19:
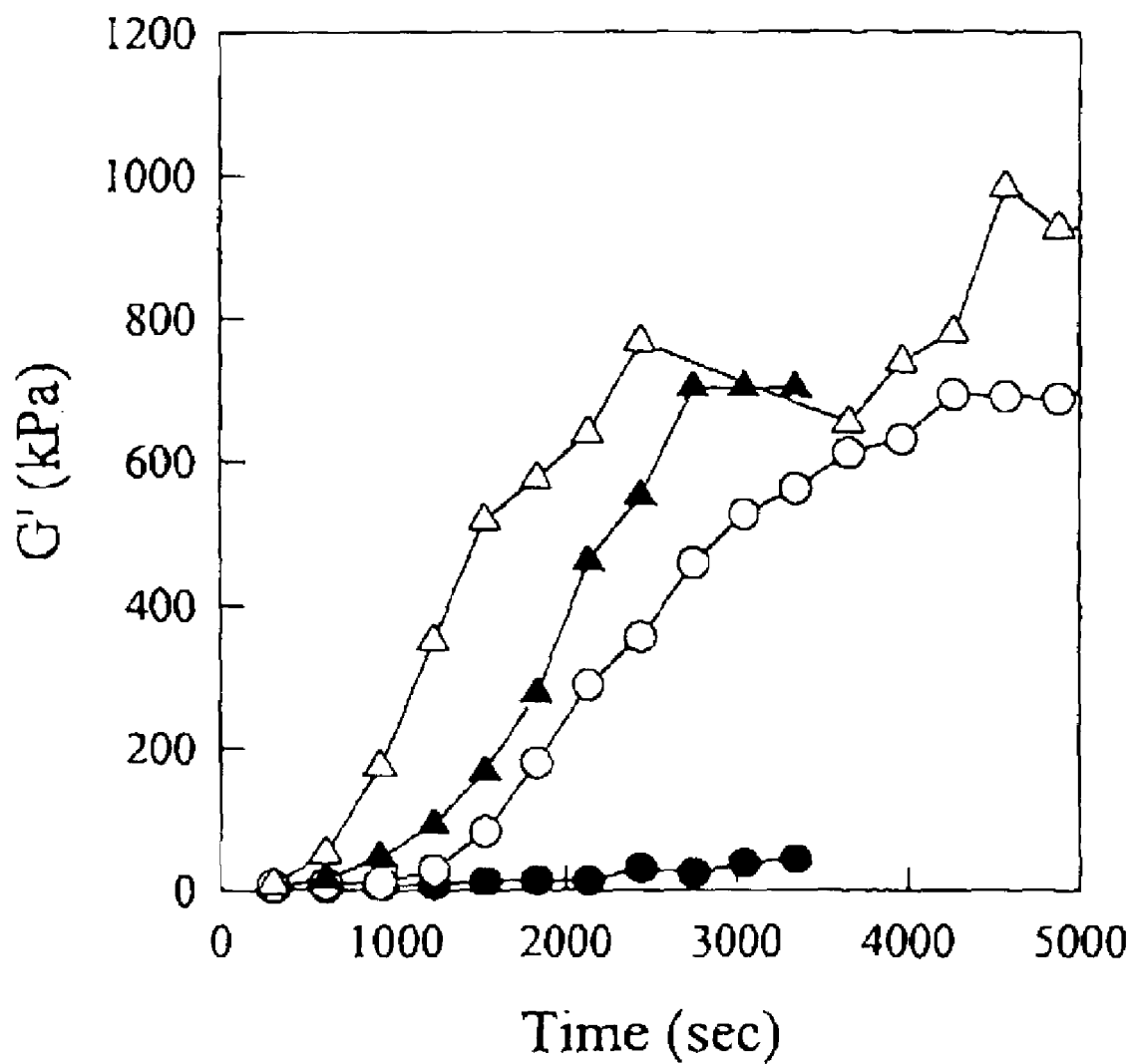

FIG. 19. Shear modulus as a function of time for a 30 v % Zirconia suspension in a 1.0 wt % (per solution weight) solution at pH 2.2 at 80° C. with various DHF concentrations ●=20 mM, ○=50 mM, ▲=80 mM, Δ=100 mM FIG. 20. Shear modulus as a function of time for a 45 v % Silicon nitride suspension in a 1.0 wt % chitosan solutions with 80 mM DHF at pH 2.0 at various temperatures ● 20° C., ○ 60° C., ▲ 80° C., Δ 98° C.

Figure 21:
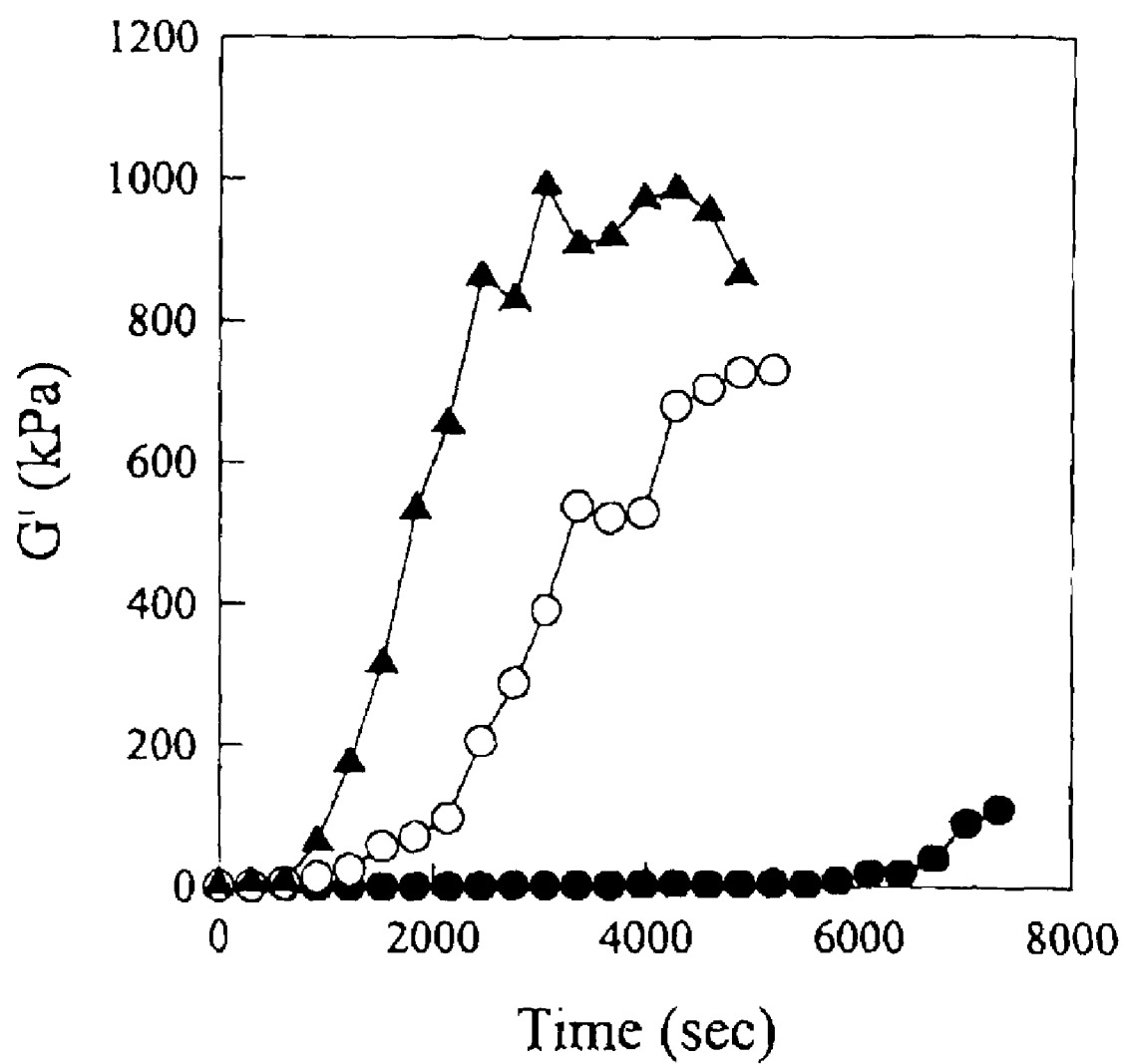

FIG. 21. Shear modulus as a function of time for a 45 v % Silicon nitride suspension in a 1.0 wt % (per solution weight) solution at pH 2.0 at 80° C. with various DHF concentrations ●=20 mM, ○=50 mM, ▲=80 mM

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Documents referred to within this specification are included herein in their entirety by way of reference.

The reference to any prior art in this specification is not, and should not be taken as, an acknowledgment or any form of suggestion that that prior art forms part of the common general knowledge in Australia.

The present invention is concerned with the formation of shaped articles which can be prepared using moulding techniques, as are well known in the art. For example the moulding techniques of the invention may include pouring the material to be moulded into a mould or use of injection moulding techniques, such as low pressure injection moulding. By using these techniques the shaped articles produced can be formed in any of a variety of shapes, which may be appropriate for use, for example, as components in machinery, as tools or household items, ornaments or works of art. This list of possibilities is, however, not intended to be limiting upon the scope of the invention. In particularly preferred embodiments of the invention the shaped articles may constitute components for use in the automotive or aeronautical industries, machine components for use in industrial processing machinery, plumbing components or electrical components. In another preferred aspect of the invention the shaped articles may in fact constitute food stuffs, food supplements or pharmaceutical formulations, such as for example controlled release pharmaceutical formulations.

The key components of the shaped articles produced according to the present invention are a solvent, a polymer and a cross-linking agent precursor. These basic constituents may have further optional components added to them depending upon the nature of the shaped article to be produced. For example, in the case of production of ceramic or metallic articles, ceramic or metallic powders such as alumina, zirconia, silica, silicon nitride, silicon carbide, aluminium nitride, ceramic superconductors and mixtures of these may be included within the solvent, polymer and cross-linking agent precursor mixture to form a suspension. Cross-linking of the polymer will form a gel, under controlled conditions, which can support the particles within their desired shape before sintering is undertaken. Similarly, in the case of foodstuffs or pharmaceutical formulations, food material components such as proteins, carbohydrates, fats and/or nucleic acids which may of course be in combination, or in the case of pharmaceutical agents or nutritional supplements, vitamins, minerals or therapeutically active agents may be included. The present invention also extends to the preparation of shaped articles which may include other biologically active agents such as herbicides, pesticides, fungicides, parasitocides, antifungal agents or antiviral agents, which are mentioned by way of example only. Such articles may, for example, be utilised to allow controlled release of agrochemicals. In some contexts it may be desired for dispersants, chelating agents, surfactants, salts, colouring agents or flavouring agents to be incorporated within the combined solvent, polymer and cross-linking agent precursor material, optionally with further components as referred to above. In the context of pharmaceutical formulations, pharmaceutically acceptable carriers and/or additives as for example disclosed in Remington's Pharmaceutical Sciences, 18th Edition, 1990, Mack Publishing Co, Easton, Pa., USA (as included herein in its entirety by way of reference) may also be included.

By way of example, the pharmaceutical agents according to the invention may include gastrointestinal agents, electrolytes and haematologic agents, cardiovascular agents, respiratory acting agents, neuroactive agents, hormones, vitamins and nutrients, enzymes, anaesthetics, sedatives, hypnotics, anti-epileptics, muscle relaxants, analgesics, antipyretics, antihistamines, parasitocides, antimicrobial agents, antibiotics, immunising agents and the like. Specific examples of these classes of pharmaceutical agent are referred to in Remington's Pharmaceutical Sciences, 18th Edition, 1990, Mack Publishing Co., Easton, Pa., USA, the disclosure of which is included herein in its entirety by way of example.

The components to be incorporated into the mould are to be combined and preferably mixed at least to some extent to ensure consistent dispersion of elements throughout the suspension, dispersion or solution, as the case may be. Although it is preferred for the combination of the components to be conducted separately, it is possible for the combination and mixture of the components to be conducted simultaneously with their placement into the mould, which of course will be generally of the shape of the shaped article which is desired to be produced.

Polymers which may be adopted in the methods according to the present invention are those which include amide, amine, carboxylic acid and hydroxyl functional groups. Examples of specific polymers which may be adopted include chitosan, polyvinylalcohol, chitin, polyacrylic acid, polyvinylacrylate, polyacrylate, polyacrylamide, xanthan gum and mixtures thereof. A particularly preferred polymer according to the present invention is chitosan. After cellulose, chitin is the most abundant polysaccharide found in nature due to its presence in crustacean shells, insect exoskeletons and fungal biomass (Mathur, et al.). Structurally, it consists primarily of 1,4-linked units of 2-acetamido-2-deoxy-β-D-glucose and, except under highly acidic conditions, is insoluble in aqueous media. The solubility of chitin can be enhanced through a process of de-acetylation, in which the N-acetyl linkage is hydrolysed under very basic conditions to produce an amine moiety. The bio-polymer chitosan results.

Chitosan can be cross-linked by di-aldehydes via by reaction of the amine moieties on the chitosan and the carbonyl group of the aldehyde, by a Schiff base reaction. For example, glutaraldehyde may be used to cross-link chitosan almost instantaneously (Thanoo, et al., 1992). This type of cross-linking does not, however, offer much control in gel formation.

The cross-linking agent precursors which may be adopted in the present invention are those which can be activated by an increase in temperature to form a cross-linking agent effective to cross-link the particular polymer or polymer mixture concerned. Preferred cross-linking agents according to the invention include ring opening molecules, and in particular the cross-linking agent precursors may be those that form a multifunctional aldehyde upon increase in temperature. Preferably the multifunctional aldehyde is a di-aldehyde which is formed from the cross-linking agent precursor when it is exposed to increased temperature.

A particularly preferred cross-linking agent precursor is 2,5-dimethoxy-2,5-dihydrofuran (DHF).

When present in acidified aqueous solution, 2,5-dimethoxy-2,5-dihydrofuran (DHF) decomposes to yield butenedial according to the scheme (Hansen, et al., 1997):

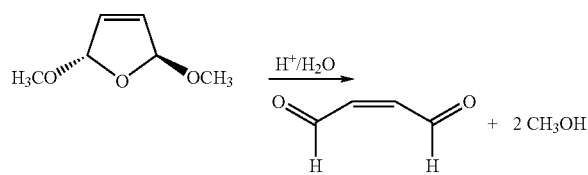

Other cross-linking agent precursors which may be adopted include any molecule which degrades with increase in temperature to produce butanedial.

Solutions of chitosan or other polymers are used as the continuous liquid phase in which the ceramic or metal powder may be dispersed. Usually between 0.1 and 8 wt % of polymer is used relative to weight of ceramic or metallic powder. Similar concentrations are typical if the polymer concentration is based on solution weight. The concentration of ceramic or metal powder in the mixture will depend on the particle characteristics, but particle concentrations near the maximum packing are usually preferred. The concentration of powder in the mixtures is typically between 20 and 75 volume percent. A relatively low viscosity (although sometimes shear thinning) suspension is produced so that the suspension may be poured or injected into the mould. FIG. 4 shows the viscosity as a function of shear rate at various pH values of a suspension suitable for moulding and gelation. The behaviour of this suspension is liquid-like and remains thus for at least one week.

When glutaraldehyde is added to the suspension containing chitosan at room temperature gelation begins immediately. Within a minute the suspension behaviour has changed from liquid-like to solid-like. In this case there is insufficient time for the suspension to be stored for any period of time before filling the mould. The use of glutaraldehyde, glyoxal, ethylene glycol diglycidyl ether, tripolyphosphate, pyrophosphate, oxalate and citrate as cross-linking agents is possible but not preferred since the gelation cannot be controlled by a triggering mechanism such as temperature.

When DHF (a ring opening cross-linking agent) is added to the powder polymer suspension the suspension remains liquid-like with a low viscosity for extended periods of time. With continuous mixing the suspension maintains a low viscosity for more than 16 hours (overnight). If left unstirred the viscosity increases slightly overnight due to slow cross-linking resulting from slow decomposition of DHF into butenedial at room temperature. This property of the temperature activated ring opening cross-linking agent is very advantageous to the economical production of defect free near net shape components, since it allows for the suspension to be stored for a period of time before mould filling, without viscosity increase. It also allows for the mould to be filled without creating defects, due to its low viscosity. High viscosity, partially gelled suspensions may lead to defects in the final component. At elevated temperatures typically between 40° C. and 98° C. the suspension gels and becomes solid-like. This behaviour is characterised by the development of and increase in the shear modulus of the suspension (See FIG. 5). This allows for the suspension to be gelled within the mould cavity to produce an elastic body with suitable strength to be removed form the mould. The rate of gelation and maximum shear modulus of the suspension can be controlled by changing the initial suspension pH. pH of between 1 and 11 may be adopted, although acidic pH is preferable. The preferred pH appears to be about pH 2 for the system investigated (See FIG. 6). Another method used to control the rate of gelation and the final gel modulus and strength is the concentration of the cross-linking agent. Generally increasing the cross-linker concentration will increase the rate of gelation and the stiffness of the gelled body formed (See FIGS. 7 and 8).

The slight shear thinning behaviour observed in FIG. 4 is due to $Al^{3+}$ ions in the solution (dissolved from the alumina particles at low pH) forming weak links between chitosan molecules. The viscosity of the suspension at room temperature (before gelation) may be further reduced by the addition of a chelating agent that binds $Al^{3+}$ ions preventing them from weakly cross-linking the chitosan. Anions such as $F^-$ and citrate have been found to be effective in this role. It should be noted that even if no chelating agent is used the links created with polyvalent ions are only weak and reversible, thus not creating a significant problem.

After preparation of a suitable suspension, solution or dispersion (as described above and as referred to in the examples below) a complex shaped article can be fabricated by transferring the suspension into a porous or non-porous mould and activating the cross-linking agent. The suspension may be transferred to the mould by pouring, vibratory filling or pressurised (low or high) injection. The mould may be an open or closed cavity mould. The mould material may be plaster, metal, ceramic or polymeric. Generally a closed cavity stiff mould with high thermal conductivity is preferred. These properties allow for quick heat transfer and good dimensional control. A closed non-porous mould prevents any drying of the body during gelation which may in some cases give rise to unwanted defects. Injecting the suspension into the mould under relatively low pressures facilitates complete filling of the mould and good dimensional control.

Heat treating the mould containing the suspension at elevated temperature causes the cross-linking agent precursor to form the active cross-linking agent which initiates the gelation. DHF and other temperature activated ring opening molecules are particularly advantageous since in the closed ring form they do not cross-link the polymer and the suspension viscosity remains low for extended periods of time, while in the opened form (at higher temperature) these molecules quickly form cross-links resulting in rapid gelation. Temperatures just below the boiling point of water produce the fastest gelation rates. Temperatures above 100° C. may be utilised if the mould is properly designed for high pressure operation. After a period of time the gelled body has sufficient mechanical integrity to be removed from the mould without damaging the component. The temperature used to initiate gelation can be varied from room temperature (approx. 20° C.) or just above to above 100° C. depending upon the desired rate of gelation, the concentration of polymer and cross-linking agent precursor, the pH, the presence of chelating agents and the extent of mixing. Preferably the gelation initiation temperature will be in the range of 40° C. to 98° C.

Numerous means can be utilised to increase the temperature of the mould and more particularly of the mould contents. For example the mould and its contents may be placed in an oven, water, oil or other solvent bath at controlled temperature, may be exposed to steam or warm air or other gas or may be exposed to radiation such as microwave radiation, ultraviolet radiation or visible light, particularly concentrated visible light. Other means of increasing the temperature of the mould contents in order to activate the cross-linking agent precursor to form the cross-linking agent itself, are of course also possible, as would be apparent to persons skilled in the art.

The mechanical behaviour of the gelled body may be controlled by such factors as the concentration of the biopolymer and cross-linker, time and temperature of heat treatment and concentration of solid particles. In some cases it may be advantageous to produce a high modulus high strength body (for example for wet green machining if desired) while in other cases a low modulus moderately strong body may be desirable. This second type of mechanical behaviour is advantageous since it produces bodies that exhibit large strain To failure ratios, which may minimise damage in mould removal. These bodies are also able to elastically return to their moulded shape after deformation during demoulding, rather than cracking.

After removal from the mould the body may be dried and fired in accordance with the methods typically used by those well skilled in the art. Difficult or costly drying or binder burnout steps are usually not required to produce high density, strong, uniform and reliable ceramic or metallic components with well controlled dimensions. With this method net shape and near net shape high performance ceramic and metallic components can be manufactured, although if necessary in particular applications some machining of the article may be required.

When the shaped articles take the form of pharmaceutical formulations they may be orally administered, for example, with an inert diluent or with an assimilable edible carrier, or may be enclosed in hard or soft shell gelatine capsule, or may be in the form of tablets. For oral therapeutic administration, the active compound may be incorporated with excipients and used in the form of ingestible tablets, pills, buccal tablets, troches, lozenges, wafers, and the like. Such compositions and preparations should contain at least 1% by weight of active compound. The percentage of the compositions and preparations may of course be varied and may conventionally be between about 5 to about 80% of the weight of the shaped article. The amount of active compound(s) in the pharmaceutical compositions is such that a suitable dosage will be obtained. Preferred compositions or preparations according to the present invention are prepared so that an oral dosage unit form contains between about 0.5 ng and 320 mg of active compound.

The tablets, troches, pills capsules and the like may also contain the following: a binder such as gum gragacanth, acacia, corn starch or gelatin; excipients such as dicalcium phosphate, a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. Various other materials may be present as coatings or to otherwise modify the physical form of the dosage unit. For instance, tablets, pills, or capsules may be coated with shellac, sugar or both. Of course, any material used in preparing any dosage unit form should be pharmaceutically pure and substantially non-toxic in the amounts employed.

The present invention will now be described further with reference to the following non-limiting examples.

EXAMPLES

Example 1

Gelation of Chitosan with DHF

The gelation by cross-linking of an aqueous chitosan/2, 5-dimethoxy-2,5-dihydrofuran (DHF) system has been rheologically examined as a function of temperature (40–98° C.), pH (0.9–3.9) and DHF concentration (1.0–10× $10^{-2}$ mole $dm^{-3}$). The resulting findings can be summarised as follows:

(1) The delay time prior to gelation decreases, and the rate of gelation increases as a function of rising temperature. The shear modulus versus time behaviour indicates that the mechanical strength of the gel initially increases then diminishes. These findings can be justified in terms of the competition between a butenedial-driven cross-linking reaction and gradual protolytic depolymerisation of chitosan. (See FIG. 1.)

(2) At pH≦2.1, both the rate of gelation and the magnitude of the maximum shear modulus increase as a function of decreasing pH. In addition, the time at which the maximum shear modulus occurs is lower for the more acidic chitosan/DHF solutions. At pH>2.1, however, more complex behaviour is observed, and can be attributed to a gradual increase in pH (and associated decrease in chitosan solubility) as the conversion of DHF into butenedial progresses. (See FIG. 2)

(3) The rate of gelation and magnitude of the maximum shear modulus increase as a function of rising DHF concentration. Such results are consistent with an increase in the rate of DHF conversion into butenedial, leading to a corresponding increase in the rate and extent of gelation (See FIG. 3.)

Example 2

Change in Rheological Behaviour of Suspension During Gelation

A high purity α-alumina powder (AKP-30) was obtained from Sumitomo Corporation (Japan). It possessed a BET surface area of 7 $m^2$ $g^{-1}$, a mean particle diameter of 0.3 μm and a density of 3.97 g $cm^{-3}$. A high molecular weight chitosan was purchased from Fluka BioChimika (Switzerland). It had a molecular weight of $2 \times 10^6$ and a degree of de-acetylation (DD) of approximately 87 per cent (Berthold, et al. 1996). The DD is an indicator of the proportion of hydrophilic (de-acylated) amine groups to hydrophobic acetamide moieties on the chitosan chains, with a high DD favouring good aqueous solubility to form low viscosity solutions. Cis/trans 2,5-dimethoxy-2,5-dihydrofuran (DHF) was obtained from Tokyo Kasei. The pH of all solutions and suspensions was adjusted using analytical grade hydrochloric acid and sodium hydroxide (both from Ajax Chemicals, Australia). All water used in this study was of Milli-Q grade (conductivity≈$10^{-6}$ S $m^{-1}$ at 20° C.).

Aqueous alumina suspensions with solids concentrations of 59 vol % were prepared by ultrasonication under acidic conditions using a Branson 450 sonifier equipped with a 0.75 inch born. The sonifier was operated at a frequency of 20 KHz, with the power output maintained at approximately 90 per cent of the limiting power (350 W). The samples were then slowly tumble-mixed for several hours prior to use.

Chitosan was initially solubilised separately from the preparation of alumina. Chitosan solutions were prepared by slowly tumble-mixing known quantities of the polysaccharide in appropriate volumes and concentrations of aqueous HCl. They were used within 12 hours of preparation in order to minimise the possibility of protolytic chitosan decomposition.

Aqueous alumina/chitosan/DHF samples for rheological analysis were prepared by mixing appropriate quantities of 59 vol % alumina suspensions, concentrated (≈2.5 wt %) chitosan solutions and pure DHF (transferred via a microsyringe). The final suspensions contained 45 vol % alumina, a solution chitosan concentration of 1.0 wt %, and solution DHF concentrations in the range of 20–200 millimole $dm^{-3}$ (mM).

Small amplitude dynamic oscillatory measurements were performed in a cone-and-plate geometry using the 'Oscillation Strain Control' function of a Stresstech Rheometer (RheoLogica Instruments, Sweden) in combination with a 4°, 30 mm cone and a concentric cylinders elevated temperature cell (CCE). Evaporation was prevented by coating the alumina/chitosan/DHF samples with a layer of high viscosity (5000 centipoise) silicone oil and sealing the sample-holding region with an insulated cover.

The results of such rheological measurements are presented in FIG. 5 for suspensions at pH 2.2 with 100 mM concentration of DHF measured at various temperatures between 20 and 98° C. This figure illustrates that at room temperature the suspension does not gel and that increasing the temperature increases the rate of gelation as well as showing the final gelled modulus of the suspension. FIG. 6 demonstrates that the gelation behaviour is a complex function of the suspension pH for various pH values of suspensions tested at 80° C. with 100 mM DHF. FIG. 7 demonstrates that the stiffness of the gelled suspension as well as the rate of gelation will be increased by increasing the concentration of the cross-linking agent DHF in suspensions tested at pH 2.2 and 80° C.

Example 3

Formation of Complex Shaped Articles

A suspension containing 45 vol % alumina, a solution chitosan concentration of 1.0 wt %, as described in Example 2. The viscosity of the suspension was measured using the 'Viscometry' function of the Stresstech rheometer, again in a cone-and-plate geometry as in Example 2. As all viscometry measurements were performed at 20° C., evaporation was not found to affect the results obtained over the experimental time-frame. The use of silicone oil was therefore not deemed to be necessary. FIG. 4 is a plot of viscosity verses shear rate for suspensions at 20° C. at various pH values from 1.1 to 4.5. This figure indicates that at room temperature the suspension is slightly shear thinning but the viscosity is relatively low. The behaviour of the suspension is liquid-like and it is pourable and injectable.

One hundred millimole $dm^{-3}$ (mM) DHF was added to the suspension. The suspension was allowed to mix for between 2 and 8 hours. The addition of the DHF and mixing did not significantly affect the rheological behaviour of the suspension.

A small die cavity (outside diameter 6.35 cm and 2.30 cm tall) was designed and fabricated out of aluminium to produce a pseudo-rotor that incorporated both varying cross section, and vane-like protrusions to demonstrate the process capability. The pseudo-rotor mould cavity outside diameter (including vanes) is 3.70 cm and its height is 1.10 cm. A second simple cylindrical mould was fabricated so cylinders could be formed to be tested for determination of the mechanical properties of the gelled bodies. The dimensions of the cylindrical cavity was 2.40 cm in diameter and 1.10 cm in thickness. A 50/50 mixture of WD-40 and silicone grease was used as a mould release agent. Only a light coating was applied.

The suspension was de-aired for 2 minutes using a siphon mechanism attached to a tap. Some small bubbles (between 0.5 and 2 mm) were observed to rise to the suspension surface and break. The suspension was then poured into the mould cavity and tapped by hand on a horizontal surface to level the suspension. Alternatively the mould cavity could be filled by injection. Once the die cavity was filled, the lid was securely fastened. The die cavity was designed to be airtight to prevent any evaporation from the suspension during gelation.

The die cavity, filled with the suspension to be gelled, was placed in a hot water bath, to initiate the gelation. The hot water bath was chosen over a dry oven due to the better heat transfer characteristics of the liquid. Specimens were heat treated at temperatures between 80 and 95° C. and times between 30 and 120 minutes. After heat treatment, the die cavity was cooled to room temperature before being opened. The mould was then opened and the sample removed. All the pseudo rotors and cylinders manufactured under these conditions had sufficient mechanical integrity to be removed from he mould and handled without damaging the component. The elastic flexibility of the parts was good (see Example 4). The details of the temperature and time of gelation for each article are given in Table I.

TABLE I

|  | Temperature | Time | Fired Density | Dry Strength | Wet Strength |
|---|---|---|---|---|---|
| Pseudo Rotor #1 | 85° C. | 60 mins. | 3.73 g/cc |  |  |
| Pseudo Rotor #2 | 95° C. | 30 mins. | 3.75 g/cc |  |  |
| Pseudo Rotor #3 | 80° C. | 120 mins. | 3.84 g/cc |  |  |
| Cylinder #1 | 85° C. | 30 mins. |  | 0.32 MPa |  |
| Cylinder #2 | 85° C. | 60 mins |  | 0.19 MPa |  |
| Cylinder #3 | 85° C. | 30 mins. |  |  | 5.8 kPa |
| Cylinder #4 | 85° C. | 60 mins. |  |  | 7.4 kPa |

The syneresis (solvent expulsion) that occurs during the gelation of the bio-polymer is an advantage of this invention since the slight shrinkage of the part causes the part to pull away from the mould wall allowing for easy mould removal and no sticking problems. Although not tested it is believed that the parts could be de-moulded without any mould lube. Too much syneresis may cause a problem in that it can lead to the development of stress and cracking in the gelled body. For this reason the concentration of the bio-polymer, cross-linking agent and particles as well as the gelation conditions such as time and temperature must be carefully controlled. The components had good surface quality replicating the shape and texture of the mould well.

The bodies were dried in air for between 16 and 36 hours and further dried at 100° C. for two hours. The total shrinkage of the parts during gelation (due to syneresis) and drying was measured to be between 5.0 and 5.5%. The weight of the parts before and after drying and the density of alumina and water were used to calculate the green density of the gelled bodies. These measurements confirmed the green density of the gelled parts was 45 V % as the suspension was formulated. The dried pseudo rotors were fired at 1450° C. for two hours in a Blue M furnace in air. FIG. 9 is a photo of the fired parts. The parts had densities ranging from 3.73 to 3.84 g/cc, corresponding to between 94 and 97% of theoretical density (see Table I). The final dimensions of the fired pseudo rotors were, 2.95 cm outer vane diameter and 0.85 cm tall. These dimensions corresponding to a total shrinkage of between 20 and 21% based on the mould dimensions.

Example 4

Strength of Wet (Saturated) and Dried Gelled Bodies

The mechanical behaviour of the bodies produced with this invention were measured utilising an Instron Dynamight 8841 test frame with a 1 kN load cell. The cylindrical specimens produced in Example 3 above were tested in diametral compression. This testing configuration produces a maximum tensile stress in the centre of the cylinder acting perpendicular to the axis of the loading and parallel to the plane in which the cylinder flat surfaces lie. With this method a tensile fracture strength of bodies can be measured without producing complex shaped tensile specimens.

Specifically Cylinders # 1 and # 2 were dried as described in Example 3 at room temperature for about 24 hours and at 110° C. for 2 hours. The specimens were allowed to cool to room temperature before testing. Cylinders #3 and #4 were tested immediately (within 1 minute) of removal from the mould. Cylinders #3 and #4 were still saturated with water when tested. The tests were conducted at a displacement rate of 0.05 mm/sec (except Cylinder #2, which was tested at 0.01 mm/sec.). The cylinder dimensions were 22.65 mm in diameter and 10.45 mm thick for the dried parts. The wet parts were probably slightly larger. FIG. 10 shows the stress-strain behaviour for the dried cylinders #1 and #2. FIG. 11 shows the stress-strain behaviour for the wet cylinders #3 and #4. The fracture strengths are indicated in the figures and Table I.

FIG. 10 indicates that the dried green strength is excellent and suitable for further dry green body processing including handling, green machining and firing. FIG. 11 indicates that the wet green parts have strength suitable for mould removal, shape retention and wet handling. One particular advantage is the large strain to failure of the wet bodies. This is manifest as greater flexibility of the part during mould removal. Such low modulus behaviour is helpful in preventing cracking when the fracture mechanism is strain controlled as may be encountered during component removal from complicated moulds.

Example 5

Effect of Crosslinker Concentration

Suspensions were produced with 45 V % AKP-30 alumina, a solution concentration of 1 wt % chitosan and different concentrations of DHF following the procedure described in Example 2. A low molecular weight chitosan (150,000 g/mole) was used instead of the high molecular weight chitosan used in previous examples. The viscosity of the alumina-chitosan-DHF suspensions was measured using a Bohlin CVO constant slow rheometer. The measurements were performed at 25° C. using a 4°, 40 mm cone and plate geometry. As shown in FIG. 12, the viscosities of all suspensions were found to be shear thinning, indicative of a slight degree of gelation of the biopolymer even prior to heat treatment. The increase of the concentration of the crosslinker (DHF) was found to increase the viscosity at all shear rates by approximately tripling the viscosity with an increase of 50 to 200 mM DHF as indicted in FIG. 13. The increase of viscosity is most likely due to the increased degree of crosslinking of the biopolymer with the greater concentrations of DHF.

Cylinders were formed from the suspensions following the procedure described in Example 3. The mechanical behaviour of the saturated cylinders was measured with an Instron Dynamite 8841 test frame in the diametral compression configuration as described in Example 4. The typical stress-strain behaviour of the saturated gelled bodies is shown in FIG. 14. The bodies exhibit significant strain to failure ratio characteristics with behaviour that is similar to a jelly (coloured, flavoured, gelatine food product). Deformation resulted in initially elastic deformation followed by plastic deformation until fracture occurred. It was not possible to distinguish between the linear and nonlinear elastic deformation or when the plastic deformation began. The large elastic flexibility of the bodies before failure give the body a resistance to fracture that is helpful in removing the body from the mould. The fracture strength increases from 50 mM to about 100 mM then tends to level off as indicated in FIGS. 13 and 14. Correspondingly, the strain to failure ratio is greatest for the 50 mM containing body but decreased and about the same for the bodies containing between 100 and 200 mM DHF. These changes in mechanical behaviour appear to be due to the greater amount of crosslinking of the biopolymer with higher concentrations of DHF. A greater degree of polymer gel crosslinking produces a stiffer gel (higher elastic modulus) and a stronger polymer network. FIG. 13 indicates that the preferred crosslinker concentration is 100 mM since this concentration produces viscosities near the minimum achievable with this chemistry, while producing gelled bodies with nearly the maximum strength attainable.

Example 6

Effect of pH

The pH of the suspensions has a complex effect on the chemical interactions between the alumina particles, chitosan and DHF (Mather et al., 1990). As pH is decreased both alumina and chitosan become increasingly positively charged. As the charge on chitosan increases its solubility increases. At pH above about 5.5 or 6 chitosan is not soluble because it has very little charge. At elevated temperature DHF decomposes to produce butenedial which is the active crosslinking agent. Both a high concentration of $H^+$ (low pH) and an increased temperature are required for DHF to produce butenedial (Hansen et al., 1997).

Suspensions were produced with 45 V % alumina, a solution concentration of 1 wt % chitosan and 200 mM DHF as described in Example 2. A low molecular weight chitosan (150,000 g/mole) was used as described in example 5. The viscosity of the suspensions prior to moulding and the strength of the gelled body were measured as described in example 5 for different pH values of the suspensions. FIG. 15 shows the results of the viscosity and strength measurements at different pH values from 4.5 to 1.5. The viscosity is a maximum at about pH 2.2 and decreases at both higher and lower pH values. A similar trend can be observed in FIG. 4 of Example 3 for suspensions containing no DHF. Although the viscosity of the suspension decreases as pH is increased the suspension appears to be less homogeneous. At pH above about 3, there appear to be chunks of undissolved chitosan in the suspension The lower amount of dissolved polymer in the solution as well as the reduced activity of the crosslinking agent (and correspondingly less crosslinking) result in the decreased viscosities at higher pH. Unfortunately the chunks of undissolved chitosan in the suspension act as defects in the gelled body (and in the final fired component) which reduce the strength and reliability of the body. FIG. 15 clearly shows the decrease in the strength of the gelled bodies as pH increases. The decreased strength is believed to he due to the defects created by the insoluble chitosan chunks as well as the reduced level of polymer crosslinking due to the reduced activity of DHF at higher pH values. The reason for the decrease in both viscosity and strength observed at pH 1.5 is currently unknown although it may be related to the high ionic strength of the very low pH condition. The greatest strength gelled bodies are produced from pH 2.2 suspensions, but there may be circumstances when the reduced viscosity of the pH 1.5 suspensions will be beneficial such as when filling complex shaped moulds.

Example 7

Effect of Time of Heat Treatment

Based on the initial rheological measurements of the alumina/chitosan/DHF system (see FIGS. 5 through 8) it was believed that increased periods of gelation up to about 5 hours would only produce stronger bodies. Surprisingly as shown in FIG. 16, the greatest strength bodies were produced after only 15 minutes of gelation. Shorter times were insufficient for enough crosslinking to occur to produce solid like bodies. Longer times produced gelled bodies that were slightly discoloured. The alumina suspensions are bright white, as were the bodies produced after 15 minutes heat treatment. Bodies produced with longer heat treatment times were slightly tan in colour. The tan colour becoming darker with longer heat treatment times. Such behaviour is most likely due to the thermal degradation of chitosan, which weakens the network strength of the parts. Another factor that might contribute to the drop in strength of the bodies is syneresis. Syneresis is the contraction of the gel and the squeezing out of free water bound from within the gel structure This phenomenon was observed in the samples with heating periods greater than 10 minutes, which indicates the presence of highly crosslinked networks. Naturally, with an increased number of crosslinks, the gelled bodies become stiffer and less deformable. These strongly gelled systems are highly susceptible to fractures leading to an apparent decrease in strength.

Example 8

Effect of Temperature of Heat Treatment

The decomposition rate of DHF into butenedial is strongly dependent upon temperature (Hansen et al. 1997). Since butenedial is the active molecule in chitosan crosslinking process, an increase in the rate of DHF decomposition will lead to an increase in the level of butenedial molecules and consequently, formation of stronger gelled bodies. Cylindrical bodies were produced and mechanically tested as described in example 5. In all cases the bodies were cooled to room temperature before de-moulding and mechanical testing. At heat treatment temperatures below 65° C., the wet gelled bodies were sticky and unable to hold their shapes. As a result, the components produced under these conditions at low heat treatment temperatures were unsuitable for mechanical testing or complex shape forming. FIG. 17 shows the results of the mechanical tests of bodies heat treated at between 65 and 85° C. Bodies produced by heat treatments at 65 to 75° C. were extremely flexible and could be deformed to a great extent without fracturing. At these treatment temperatures much of the deformation was permanent. By increasing the operating temperature, the gelation process completed after a shorter period of time and samples became relatively more rigid, allowing successful mould removal and handling at heat treatment temperatures of 85° C. and above.

Example 9

Zirconia Suspension

A high purity Zirconia powder (TZ-O) was obtained from Tosoh Corporation (Japan). It possessed a surface area of 15.9 m$^2$/g, with a crystalline size of 250 Å. A high molecular weight chitosan was obtained from Fluka Biochimika (Switzerland). It has a molecular weight of 2×10$^6$. Cis/trans 2,5-dimethoxy-2,5-dihydrofuran (DHF) was obtained from Tokyo Kasei. The pH of all solutions and suspensions was adjusted using analytical grade hydrochloric acid and sodium hydroxide. All water used in this study was of triple distilled grade.

Chitosan stock solution was made at 2.0 weight %, in triple distilled water. The chitosan powder was mixed into water, with an overhead mixer, while the pH of the solution was constantly adjusted to 2.0, with appropriate volume of aqueous HCl. The solutions were used within 24 hours of preparation.

Aqueous zirconia/chitosan/DHF samples for rheological analysis were prepared by mixing appropriate quantities of zirconia, chitosan solutions and pure DHF (transferred via micropippette) with a spatula. The final suspension contained 30 vol % Zirconia, chitosan concentration of 1 wt %, and solution DHF in the range of 20-100 millimole dm$^{-3}$ (mM).

Small amplitude dynamic oscillatory measurements were performed in a cone-plate geometry using the 'Oscillation function' of the Carri-med Constant Stress Rheometer with a 4 cm, 1 59° cone. Evaporation was prevented by sealing the Zirconia/chitosan/DHF sample with a layer of paraffin oil.

The results of such rheological measurements are presented in FIG. 18 for suspensions at pH 2.2 with 80 mM concentration of DHF measured at various temperatures between 20 and 98° C. This figure illustrates that at room temperature, the suspension does not gel and that increasing the temperature increases the rate of gelation and the final shear modulus of the suspension. FIG. 19, demonstrates that the shear modulus and rate of gelation increased with concentration of DHF.

Example 10

Silicon Nitride Suspension

Silicon nitride powder (SN-E03) was obtained from UBE INDUSTRIES LTD (Japan) It possessed a surface area of 3.2 m$^2$/g. A high molecular weight chitosan was obtained from Fluka Biochimika (Switzerland). It has a molecular weight of 2×10$^6$. Cis/trans 2,5-dimethoxy-2,5-dihydrofuran (DHF) was obtained from Tokyo Kasei. The pH of all solutions and suspensions was adjusted using analytical grade hydrochloric acid and sodium hydroxide. All water used in this study was of triple distilled grade.

Chitosan stock solution was made at 2.0 weight %, in triple distilled water. The chitosan powder was mixed into water, with an overhead mixer, while the pH of the solution was constantly adjusted to 2.0, with appropriate volume of aqueous HCl. The solutions were used within 24 hours of preparation.

Aqueous silicon nitride/chitosan/DHF samples for rheological analysis were prepared by mixing appropriate quantities of silicon nitride, chitosan solutions and pure DHF (transferred via micropippette) with a spatula. The final suspension contained 30 vol % silicon nitride, chitosan concentration of 1 wt %, and solution DHF in the range of 20–100 millimole dm$^{-3}$ (mM).

Small amplitude dynamic oscillatory measurements were performed by cone-plate geometry using the 'Oscillation function' of the Carri-med Constant Stress Rheometer with a 4 cm, 1 59° cone. Evaporation was prevented by sealing the silicon nitride/chitosan/DHF sample with a layer of paraffin oil.

Figure 20:
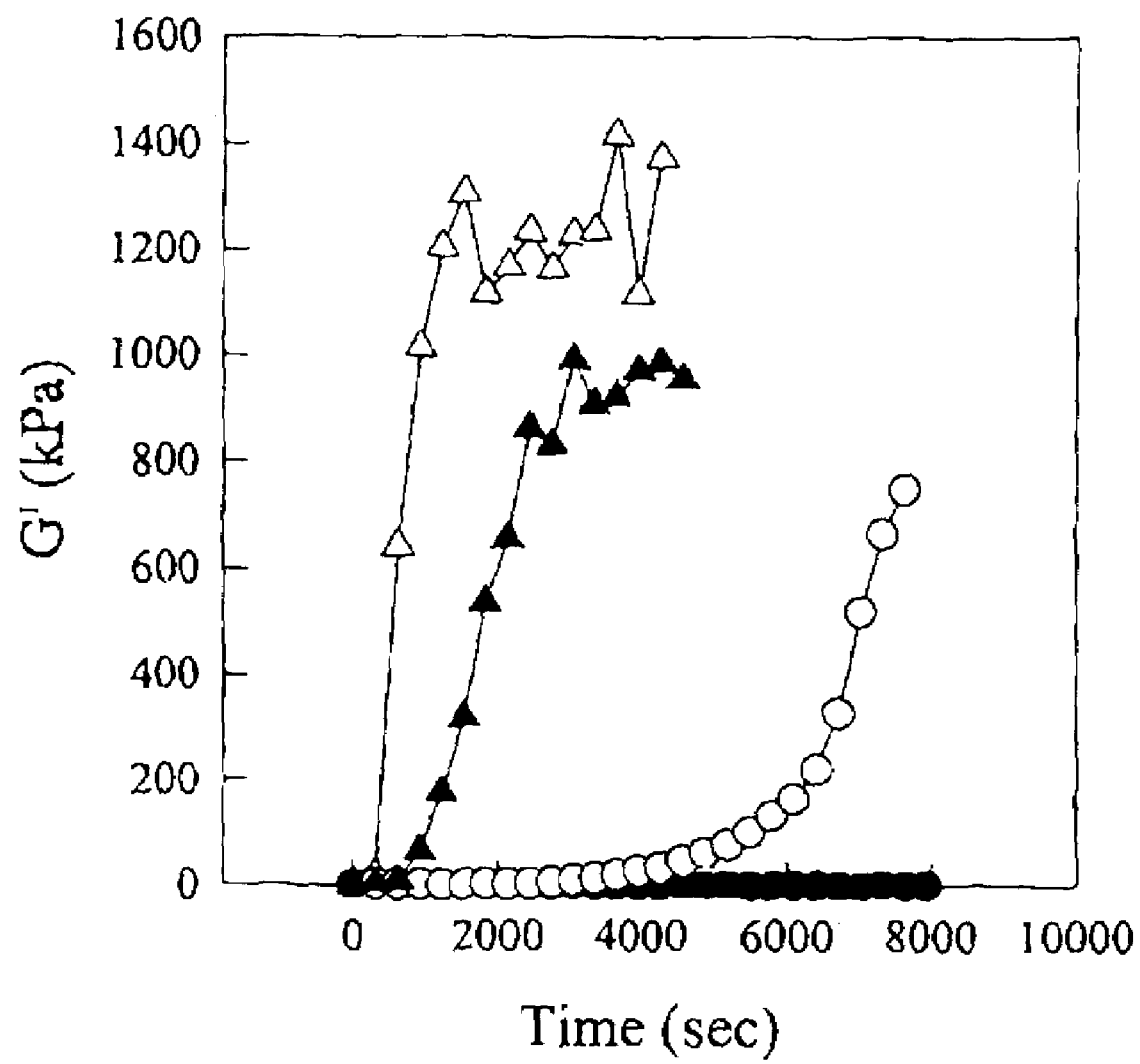

The results of such rheological measurements are presented in FIG. 20 for suspensions at pH 2,0 with 80 mM concentration of DHF measured at various temperatures between 20 and 98° C. This figure illustrates that at room temperature, the suspension does not gel and that increasing the temperature increases the rate of gelation and the final shear modulus of the suspension. FIG. 21, demonstrates that the shear modulus and rate of gelation increased with concentration of DHF.

It is to be understood that the present invention has been described by way of example only and that modifications and/or alterations thereto, which would be apparent to a person skilled in the art based upon the disclosure herein, are also considered to fall within the scope and spirit of the invention.

REFERENCES

Balzer, B., Hruschka, M. K. M., and Gauckler, L. J., J. Colloid and Interface Sci., 216, 379–386 (1999).

Berthold, A., Cremer, K., and Kreuter, J., "Preparation and Characterization of Chitosan Microspheres as Drug Carrier for Prednisolone Sodium Phosphate as Model for Anti-Inflammatory Drugs," J. Control Rel., 39, 17–25, (1996).

Chen, Y., Xie, Z Z Z, Yang, J., and Huang, Y., J. European Ceramic Soc., 19, 271–275 (1 999).

German, R. M., Hens, K. F. and Lin, S. -T. P., "Key Issues in Powder Injection Moulding", Am. Ceram. Soc. Bulletin, 70 [8] 1294–1302 (1991)

Hansen, E. W.; Holm, K. H.; Jahr, D. M., Olafsen, K.; Stori, A., Polymer, 38, 4863–4871 (1997).

Lange, F. F., "Powder Processing Science and Technology for Increased Reliability". J. Am. Ceram. Soc., 72 [1] 3–15 (1989).

Mangels, J. A., "Low Pressure Injection Moulding", Am. Ceram. Soc. Bull., 73, 37–41 (1994).

Mathur. N. K.; Narang, C. K. J. Chem. Edu. 67, 938–942 (1990)

Pujari, V. K, Tracey, D. M., Foley, M. R., Paille. N. I., Pelletier, P. J. Sales, L. C., Willkens, C. A. and Yeckley, R. L., "Reliable Ceramics for Advanced Heat Engines", Am. Ceram. Soc. Bulletin, 74 [4] 86–90 (1995).

Takeshita, M. and Kurita. S., "Development of Self Hardening Slip Casting", J. europ. Ceram. Soc., 17, 415–419 (1997).

Thanoo, B. C., Sunny, M. C., and Jayakrishnan, A. J., Pharm. Pharmacol. 44, 283–286 (1992).

The disclosure of each of the above publications, which are referred to within this specification, is included herein in its entirety, by way of reference.

The invention claimed is:

1. A method of forming a shaped article comprising the steps of:
   (a) combining solvent, polymer, cross-linking agent precursor and optional further components and placing into a mould of desired shape;

(b) increasing temperature of mould contents to activate cross-linking agent;
(c) allowing mould contents to solidify to sufficient extent to form a shaped article; and
(d) removing the shaped article from the mould;
wherein the cross-linking agent precursor forms a multi-functional aldehyde upon temperature increase.

2. The method according to claim 1 wherein the polymer is selected from the group chitosan, polyvinylalcohol, chitin, polyacrylic acid, polyvinylacrylate, polyacrylamide, pectin, xanthan gum, polymers having amide, carboxylic acid and/or hydroxyl functionalities, and mixtures thereof.

3. The method according to claim 1 wherein the cross-linking agent precursor forms a di-aldehyde upon temperature increase.

4. A method of forming a shaped article comprising the steps of:
(a) combining solvent, polymer, cross-linking agent precursor and optional further components and placing into a mould of desired shape;
(b) increasing temperature of mould contents to activate cross-linking agent;
(c) allowing mould contents to solidify to sufficient extent to form a shaped article; and
(d) removing the shaped article from the mould,
wherein the cross-linking agent precursor is 2,5-dimethoxy-2,5-dihydrofuran (DHF).

5. The method according to claim 1 wherein the mould is filled by pouring or by injection.

6. The method according to claim 1 wherein the solvent is selected from water, ethanol, methanol, iso-propanol and mixtures thereof.

7. The method according to claim 1 wherein the optional further components include ceramic or metallic powders.

8. The method according to claim 7 wherein the ceramic or metallic powder is selected from alumina, zirconia, silica silicon nitride, silicon carbide, aluminum nitride and mixtures thereof.

9. The method according to claim 1 wherein the optional further components include one or more pharmaceutical substances.

10. The method according to claim 1 which includes further drying and/or firing steps.

11. The method according to claim 1 wherein the optional further components include one or more of dispersants, chelating agents, surfactants, salts, colouring agents and biologically active agents.

12. The method according to claim 1 wherein the shaped article is net shape or near net shape.

13. The method according to claim 1, comprising allowing mould contents to solidify to sufficient extent to form a cross-linked shaped article in the mould.

14. The method according to claim 9, wherein the optional further components include one or more active pharmaceutical compounds.

* * * * *